United States Patent
Haubold et al.

(10) Patent No.: US 7,241,399 B2
(45) Date of Patent: Jul. 10, 2007

(54) SYNTHESIS OF NANOPARTICLES

(75) Inventors: Stephan Haubold, Hamburg (DE); Markus Haase, Hamburg (DE); Karsten Riwotzki, Hamburg (DE); Horst Weller, Hamburg (DE); Heike Meyssamy, Hamburg (DE); Fernando Ibarra, Hamburg (DE)

(73) Assignee: Centrum fuer Angewandte Nanotechnologie (CAN) GmbH, Hamburg (DE)

( * ) Notice: Subject to any disclaimer, the term of this patent is extended or adjusted under 35 U.S.C. 154(b) by 0 days.

(21) Appl. No.: 10/129,530

(22) PCT Filed: Sep. 7, 2001

(86) PCT No.: PCT/DE01/03433

§ 371 (c)(1),
(2), (4) Date: Jun. 26, 2002

(87) PCT Pub. No.: WO02/20696

PCT Pub. Date: Mar. 14, 2002

(65) Prior Publication Data

US 2003/0032192 A1     Feb. 13, 2003

Related U.S. Application Data

(63) Continuation-in-part of application No. PCT/DE00/03130, filed on Sep. 8, 2000.

(51) Int. Cl.
- *C09K 11/08* (2006.01)
- *G01N 21/91* (2006.01)
- *G01N 21/76* (2006.01)
- *G07D 7/00* (2006.01)
- *C09D 11/00* (2006.01)

(52) U.S. Cl. ............... 252/301.4 R; 428/403; 106/401; 356/433; 356/243.1; 356/951; 252/301.4 P; 252/301.5; 252/301.4 S; 252/301.6 S; 252/301.6 R; 252/301.6 P; 252/301.6 H; 252/301.4 F; 252/301.6 F

(58) Field of Classification Search ......... 252/301.4 R, 252/301.4 P, 301.4 F, 301.4 H, 301.5, 301.6 R, 252/301.6 P, 301.6 H, 301.6 S, 301.4 S; 423/263, 305, 321, 279, 326, 330.1, 331, 423/332, 333, 409, 411, 412, 463, 466, 464, 423/489, 490, 491, 492, 493, 494, 495, 497, 423/499.1, 499.3, 509, 517, 541.1, 544.1, 423/544.3, 600, 594.6, 594.9, 594.13; 428/403, 428/404; 106/401
See application file for complete search history.

(56) References Cited

U.S. PATENT DOCUMENTS 3,886,083 A    5/1975    Laxer (Continued)

FOREIGN PATENT DOCUMENTS

DE    19738544    3/1999

(Continued)

OTHER PUBLICATIONS

Inoue et al, "Synthesis of Yttrium Aluminum Garnet by Glycothermal Method", 1991.*

(Continued)

*Primary Examiner*—C. Melissa Koslow
(74) *Attorney, Agent, or Firm*—Greenblum & Bernstein, P.L.C.

(57) ABSTRACT

Methods for the preparation of inorganic nanoparticles capable of fluorescence, wherein the nanoparticles consist of a host material that comprises at least one dopant. The synthesis of the invention in organic solvents allows to gain a considerably higher yield compared to the prior art synthesis in water. All kinds of objects can advantageously be marked and reliably authenticated by using an automated method on the basis of a characteristic emission. Further, the size distribution of the prepared nanoparticles is nartower which renders a subsequent size-selected separation process superfluous.

41 Claims, 4 Drawing Sheets

U.S. PATENT DOCUMENTS

| | | | |
|---|---|---|---|
| 4,238,524 | A | 12/1980 | LaLiberte et al. |
| 4,331,871 | A | 5/1982 | Allinikov |
| 4,700,657 | A | 10/1987 | Butland |
| 5,413,736 | A * | 5/1995 | Nishisu et al. ........ 252/301.4 R |
| 5,418,855 | A | 5/1995 | Liang et al. |
| 5,472,477 | A * | 12/1995 | Konig ........................ 75/343 |
| 5,505,928 | A * | 4/1996 | Alivisatos et al. .......... 423/299 |
| 5,637,258 | A * | 6/1997 | Goldburt et al. ...... 252/301.4 R |
| 5,751,018 | A | 5/1998 | Alivisatos et al. |
| 5,893,999 | A * | 4/1999 | Tamatani et al. ..... 252/301.4 R |
| 6,103,868 | A | 8/2000 | Heath et al. |
| 6,203,726 | B1 | 3/2001 | Danielson et al. |
| 6,225,198 | B1 | 5/2001 | Alivisatos et al. |
| 6,251,303 | B1 * | 6/2001 | Bawendi et al. ...... 252/301.4 R |
| 6,299,797 | B1 * | 10/2001 | Igarashi et al. ....... 252/301.4 R |
| 6,309,701 | B1 | 10/2001 | Barbera-Guillem |
| 6,316,377 | B1 | 11/2001 | Fulton et al. |
| 6,379,583 | B1 * | 4/2002 | Gray et al. ........... 252/301.4 R |
| 6,391,273 | B1 * | 5/2002 | Konrad et al. .............. 423/263 |
| 6,515,314 | B1 * | 2/2003 | Duggal et al. .............. 257/184 |
| 6,531,074 | B2 * | 3/2003 | Trumble et al. ...... 252/301.4 R |
| 6,576,155 | B1 * | 6/2003 | Barbera-Guillem .... 252/301.36 |
| 6,576,156 | B1 * | 6/2003 | Ratna et al. .......... 252/301.4 R |
| 2002/0071952 | A1 * | 6/2002 | Bawendi et al. ............ 428/403 |
| 2002/0179886 | A1 * | 12/2002 | Kumar ................. 252/301.4 R |
| 2004/0014060 | A1 * | 1/2004 | Hoheisel et al. ................ 435/6 |
| 2004/0156784 | A1 * | 8/2004 | Haase et al. ................ 424/9.32 |

FOREIGN PATENT DOCUMENTS

| | | |
|---|---|---|
| JP | 2000104058 | 4/2000 |
| JP | 2000256251 | 9/2000 |
| WO | 98/20365 | 5/1998 |
| WO | 99/37814 | 7/1999 |
| WO | 00/17103 | 3/2000 |
| WO | 00/17655 | 3/2000 |
| WO | 00/38282 | 6/2000 |
| WO | WO 00/38282 * | 6/2000 |
| WO | 00/56837 | 9/2000 |
| WO | WO 00/56837 * | 9/2000 |

OTHER PUBLICATIONS

Inoue et al, "Synthesis of Submicron Spherical Crystals of Gadolinium Gallium Garnet by the Glycothermal Method", 1995.*

Inoue et al, "Synthesis of Rare-Earth Gallium Garnets by the Glycothermal Method", 1998.*

Meyssamy et al, Wet-Chemical Synthesis of Doped Colloidal Nanomaterials: Particles and Fibers of LaPO4:Eu, LaPO4:Ce, an LaPO4:Ce,Tb, 1999.*

Riwotzki et al , "Liquid-Phase Synthesis of Doped Nanoparticles: Colloids of Luminescing LaPO4:Eu and CePO4:Tb Particles with a Narrow Size Distrubtion", Apr. 6, 2000.*

Haase et al, "Synthesis and Properties of Colloidal Lanthanide-Doped Nanocrystals", May, 2000.*

English language abstract of CN 1193640.

K. Riwotzki et al., "Liquid-Phase Synthesis of Doped Nanoparticles: Colloids of Luminescing $LaPO_4$:Eu and $CePO_4$:Tb Particles with a Narrow Particle Size Distribution" J. Phys. Chem. B, vol. 104, No. 13, pp. 2824-2828 (2000).

M. Haase et al., "Synthesis and Properties of Colloidal Lanthanide-doped Nanocrystals" Journal of Alloys and Compounds 303-304, pp. 191-197 (2000).

Heike Meyssamy et al., "Wet-Chemical Synthesis of Doped Nanoparticles: Particles and Fibers of $LaPO_4$:Eu, $LaPO_4$:Ce and $CePO_4$:Ce,Tb" Advanced Materials, vol. 11, No. 10, pp. 840-844 (1999).

Masashi Inoue et al., "Synthesis of Rare-Earth Gallium Garnets by the Glycothermal Method" Journal of the American Ceramic Society, vol. 81, No. 5, pp. 1173-1183, (May 1998).

M. Inoue et al., "Synthesis of Submicron Spherical Crystals of Fadolinium Gallium Garnets by the Glycothermal Method" Journal of Materials Science Letter, vol. 14, pp. 1303-1305, (1995).

Masashi Inoue et al., "Synthesis of Yttrium Aluminum Garnet by Glycothermal Method" Journal of the American Ceramic Society, vol. 74, No. 6, pp. 1452-1454, (Jun. 1991).

M. Inoue et al., "Reactions of Rare Earth Acetates with Aluminum Isopropoxide in Ethylene Glycol: Synthesis of the Garnet and monoclinic Phases of Rare Earth Aluminates" Journal of Materials Science, vol. 33, pp. 5838-5841 (May 1998).

Peter J. Dobson, "Nanoparticles and Noanocomposites", Paper for "Commercial and Industrial Application for . Microengineering and Nanotechnology" Apr. 26, 1999, London.

Abstract of Y Xie et al., "Solvothermal Route to Nanocrystalline CdSE" Journal of Solid State Chemistry, Oct. 1999, Academic Press, USA, abstract only.

* cited by examiner

SYNTHESIS OF NANOPARTICLES

The present application is a national stage of International Application No. PCT/DE01/03433, filed Sep. 7, 2001, which was not published in English under PCT Article 21(2), which is a Continuation-in-Part of International Application No. PCT/DE00/03130, filed Sep. 8, 2000, which was not published in English under PCT Article 21(2).

PRIOR ART

The present invention relates to methods for the synthesis of nanoparticles, in particular of metal salt nanoparticles. The invention also relates to the preparation of nanoparticles capable of fluorescence as well as to the preparation of doped nanoparticles.

Metal salt nanoparticles in the sense of the present invention comprise a crystal lattice or, in case of a doping, a host lattice. The cation of the lattice is a metal, particularly a metal of the third subgroup of the periodic system, for example lanthanum, or a rare earth metal. The anion of the lattice, e.g. $PO_4^{3-}$, is obtained from a suitable anion source, for example from a free acid of the salts of the particular nanoparticles that are to be prepared, e.g. lanthanum phosphate nanoparticles.

The closest prior art for the synthesis of these metal salt nanoparticles is the scientific publication 'Wet-Chemical Synthesis of Doped Colloidal Nanamaterials: Particles and Fibres of $LaPO_4$:Eu, $LaPO_4$:Ce, and $LaPO_4$:Ce,Tb' by Messamy H., Riwotzki K., Kornowski A., Naused S., and Haase M., published on Jul. 5th, 1999, in Advanced Materials (1999), Vol. 11, No. 10, p 840ff. Using a wet-chemical synthesis of the starting materials in water (hydrothermal synthesis) it is possible to make undoped or doped nanoparticles, particularly the above-named metal salt nanoparticles, as colloidal solution in water. Further steps of the method include precipitation followed by centrifugation which allows the preparation of a solid as a concentrate.

The hydrothermal synthesis of the above-named method, however, results basically in a relatively broad distribution of particle sizes and thus in a poor yield of particles of a certain (desired) size. In the above-named method, the percentage of nanoparticles with diameters of less than 25 nm for example (these are the usable particles) is around 20% as measured by comparing the amount of usable particles with the total amount of crystalline substance that is produced by the method. Moreover, because water is used as synthesis medium, an autoclave is necessary to maintain the high pressure during the reaction. This is regarded to be a disadvantage at least for an industrial production of the final substance. It is therefore desirable to increase the yield and to facilitate the synthesis in the laboratory as well as for a production on an industrial scale.

However, due to the ever-increasing possibilities for the application of nanoparticles, a more simple and more efficient preparation is desired not only for the above-named lanthanum phosphate nanoparticles but also for a large group of nanoparticles of which the crystal lattice or host lattice can include compounds particularly from the group of phosphates, halophosphates, arsenates, sulphates, borates, aluminates, gallates, silicates, germanates, oxides, vanadates, niobates, tantalates, tungstates, molybdates, alkalihalogenates, other halogenides, nitrides, sulphides, selenides, suiphoselenides, as well as oxysuiphides.

With respect to the particular aspects of the doping of nanoparticles and of the capability of nanoparticles to fluoresce, the above-named publication from Jul. 5th, 1999, shows a way to produce inorganic fluorescent dyes which have a much higher long-term stability than conventional organic fluorescent dyes. The nano-phosphate particles named in the title of the publication are doped specifically with lanthanide ions which give fluorescent properties to the particles.

A substance is thus known where the beneficial property of long-term stability due to the inorganic nature of the dye is taken advantage of. However, the above-named disadvantages of the hydrothermal synthesis have to be accepted, particularly the requirement of high pressure and a low yield.

Prior art, cited below, is further to use fluorescent dyes for example to label cheques, as described in the U.S. Pat. No. 3,886,083, as security inks, as disclosed in the Chinese patent CN 1,193,640, to detect tears in surfaces, as described in U.S. Pat. No. 4,331,871, to detect fingerprints, see U.S. Pat. No. 4,700,657, further to mark clear plastic objects such as glasses and contact lenses and other products, see U.S. Pat. Nos. 4,238,524 and 5,418,855, as well as to detect leaks, see WO 9 820 365. However, in these publications, the fluorescent dyes are organic substances.

Disadvantages of the described organic dyes are their insufficient stability and, as a result, their tendency to fade, the often short distance between the wavelengths of exciting and emitted light which causes problems when distinguishing the emitted light from the excitation light, further the colourfullness of the employed dyes under normal light which has an disturbing effect on either the design of the fluorescent product or the security of the marking, poor chemical stability against external influences which restricts the field of application of the dyes, and often poor transparency of the dyes in connection with clear plastic materials, windows and security markings on all objects that have to do justice to a high demand on security. For example, these are cheque cards, credit cards, customer cards, automobile markings, markings on valuable objects such as jewellery, works of art; further such products that have the purpose to unambiguously identify the manufacturer without showing this externally to the customer or a potential counterfeiter.

Nanoparticles are also used as possible carriers for fluorescent dyes, for example after it has been recognized from the disclosure of WO 9937814 that it is of disadvantage to couple the fluorescent dyes only by one bond to the surface of the respective carrier materials. The important dyes are thus susceptible to environmental influences, and chemical reactions such as oxidation and reduction can slightly weaken their effect. Exactly this should be avoided as a matter of principle because the most cases of application require a long-term stability of the fluorescence.

The above-mentioned WO 9937814 describes a way to prepare even multi-coloured fluorescence. First, polymeric microparticles are synthesized which carry polymeric nanoparticles which for their part are steeped in fluorescent organic dyes out of the generally known class of cyanine dyes. That is, dyed nanoparticles are incorporated into porous microparticles. Several dyes can be used simultaneously to produce different colours through the fluorescence emission of the microparticles. The microparticles and nanoparticles exhibit a non-smooth surface preferably by additional functional groups on the respective surfaces in order to facilitate binding. The resulting carriers have large surfaces that are able to bind many nanoparticles and dyes, respectively, at the periphery of the microparticles and partly in the regions lying slightly further inside.

However, a disadvantage of this method is that it uses organic fluorescence materials which—despite the at least partial incorporation into microparticles—are prone to premature ageing and wear as already mentioned and thus display a poor long-term stability.

A major disadvantage of the use of organic dyes is that they can be destroyed when the excitation is unadjusted and too strong, and that they loose their colour effect.

A further disadvantage is that such substances show the phenomenon of the so-called 'concentration quenching'. That means, if the fluorescent particles are too concentrated, for example in form of a powder, then they re-absorb large parts or all of the emitted fluorescence. An organic fluorescent dye in form of a powder therefore glows badly. This property is very disadvantageous because the intensity of the fluorescence that can maximally be reached is limited by concentration quenching.

A further disadvantage is that these organic fluorescent dyes are not suitable, i.e. not flexible enough for the special requirements of many application examples, for the use of marking objects.

OBJECTIVE OF THE INVENTION

Thus the objective of the invention is to provide an organic synthesis method for nanoparticles of the substance groups mentioned at the beginning under avoidance of the disadvantages of a hydrothermal synthesis.

SUMMARY AND ADVANTAGES OF THE INVENTION

The following passage shall refer to the claims.

Compared to the method that is described in the publication mentioned at the beginning, the method according to the present invention exhibits the advantage of gaining a considerably higher yield. The reason for this lies in a much narrower size distribution of the prepared nanoparticles which renders a subsequent size-selective separation superfluous.

Further, a teaching of a synoptic nature is disclosed whereof the universal approach allows to overcome each of the individual difficulties in synthesizing nanoparticles from distinct, desired nanoparticle substance groups by using specific approaches of the invention that will immediately be apparent from the synoptic teaching.

This teaching of the invention is independent of whether doped or undoped nanoparticles are being prepared. As far as embodiments for the synthesis of doped nanoparticles are given, it is to be understood that the instruction for the preparation of corresponding undoped nanoparticles can essentially be obtained by replacing the starting material required for the doping with an equivalent amount of starting material for the host lattice material. Further, the term 'doping' is used herein in a very broad sense so that it is not limited by a certain maxi percentage of the lattice positions for the dopant. For example, it also includes reference to nanoparticles build of mixed phosphates, or other nanoparticles, such as nanoparticles that show parity of moieties of two or more cations.

In the most general aspect of the invention, a method is disclosed for synthesizing metal salt nanoparticles, comprising a crystal lattice or host lattice of which the cation is capable of being produced from a cation source and of which the anion is capable of being produced from a class of substances that serves as an anion source, in which method the host material can include compounds particularly from the group consisting of phosphates, halophosphates, arsenates, sulphates, borates, aluminates, gallates, silicates, germanates, oxides, vanadates, niobates, tantalates, tungstates, molybdates, alkalihalogenates, other halides, nitrides, sulphides, selenides, sulphoselenides, as well as oxysulphides, the method being characterized by the following steps:

a) preparation of a synthesis mixture, at least from aa) an organic solvent which comprises at least one component controlling the crystal growth of the nanoparticles, in particular a component comprising a phosphororganic compound, or an amine compound, in particular a monoalkylamine, particularly dodecylamine, or a dialkylamine, particularly bis(ethylhexyl)amine, in particular for zinc comprising nanoparticles, bb) a cation starting material which serves as cation source and which is soluble or at least dispersible in the synthesis mixture, particularly a metal salt starting compound, preferred a metal chloride or an alkoxide, or a metal acetate, and cc) an anion starting material that serves as anion source, which is soluble or at least dispersible in the synthesis mixture and which is selected from said class of substances, said class of substances comprising:

aaa) free acids of the salts of the particular metal salt nanoparticles which are to be prepared, or bbb) salts that are soluble or at least dispersible in the synthesis mixture, in particular salts with an organic cation, or metal salts, the latter preferably being alkali metal salts, or ccc) organic compounds which release the anion beyond an increased synthesis minimum temperature, and a suitable, anion-donating substance is selected from the class of substances depending on a respective selection of the salt of the nanoparticles to be prepared, and b) keeping the mixture at a predetermined synthesis minimum temperature during a synthesis period appropriate for said temperature.

Thus, in the most general aspect of the present invention concerning the preparation technique, a broadly applicable approach is disclosed that makes it possible to synthesize diverse metal salt nanoparticles and even for the first time to synthesize certain semiconductor nanoparticles.

In addition, it is possible to prepare very small fluorescent nanoparticles. They have a diameter of only a few nanometers and they allow a homogenous integration into most delicate films, most delicate coatings, a good solubility in solvents without any sedimentation of certain parts at the bottom of the solution that is typical for particles with larger sizes, or a homogenous thorough mixing with fine, dust-like powders. Using these nanoparticles, there is no detectable change in the material regarding the respective carrier substances.

Finally, the preparation method is much less risky for many of the substances claimed and presented in this invention because it can be carried out without excess pressure and without the use of an autoclave.

Preferably, the basic synthesis method can be used, wherein a) phosphoric acid is used as anion source for the preparation of nanoparticles with phosphorus-containing anions, wherein boric acid is used as anion source for the preparation of nanoparticles with boron-containing anions, wherein hydrofluoric acid is used as anion source for the preparation of nanoparticles with fluorine-containing anions, wherein b) in case of using a salt of the anion substance class and an organic cation, a salt and a trialkylammonium or tetraalkylammonium cation are used. For example, to prepare nanoparticles with phosphate-containing anions, tetrabutylammonium dihydrogenphosphate, tetramethylammonium dihydrogenphosphate, or triethylammonium dihydrogenphosphate are used as anion source; to prepare nanoparticles with sulphate-containing anions, tetrabutylammonium hydrogensulphate, tetramethylammonium hydrogensulphate, bis-tetrabutylammonium sulphate, or triethylammonium hydrogensulphate are used; to prepare nanoparticles with fluorine-containing anions, triethylamine-trishydrofluoride, pyridine hydrofluoride, or collidine hydrofluoride are used; and to prepare nanoparticles with sulphide-containing anions, collidine hydrosulphide is used as anion source. In case of employing a salt of the anion substance class that is sparingly soluble in the synthesis mixture, a complexing agent for the metal component of the metal salt is preferably added to the synthesis mixture in order to improve the solubility of the salt; for alkali metal salts, this complexing agent is preferably a crown ether.

In case of using an anion-donating, organic compound that is degraded at higher temperatures, an ester, that has been determined in advance, of the acid corresponding to the particular anion that has been chosen can preferably be used. Suitable is an ester of an alcohol which tends to an elimination reaction at higher temperatures (that is, under the conditions of the synthesis) and thus cleaves off water. Examples for such alcohols are 2-methyl-2-propanol, 2-butanol, and 2-methyl-2-butanol.

A phosphoric ester can be used for phosphates, a silicic acid ester for silicates, a boric acid ester for borates, a sulphuric acid ester for sulphates, a vanadic acid ester for vanadates, a tungstic acid ester for tungstates.

A mixture of triethylammonium dihydrogenphosphate and triethylamine trihydrogenfluoride, both commercially available, can for example be used for halophosphates.

By analogy, it is possible to use unstable alkaloids as anion-donating substance preferably for niobates, tantalates, aluminates, gallates, arsenates, and germanates.

Apart from the metal salts, bis-trimethylsilyl sulphide can also be used as anion-donating substance for sulphides. By analogy, bis-trimethylsilyl selenide is suitable for selenides, and an appropriate mixture of the above substances for sulphoselenides.

As a phosphororganic compound that is the responsible component for controlling particle growth, at least one of the following substances can preferably be included in the solvent:

a) esters of phosphinic acid, $((R_1\!-\!)(R_2\!-\!)(R_3\!-\!O\!-\!)P\!=\!O)$, b) diesters of phosphonic acid, $((R_1\!-\!)(R_2\!-\!O\!-\!)(R_3\!-\!O\!-\!)P\!=\!O)$, c) triesters of phosphoric acid (trialkyl phosphates), $((R_1\!-\!O\!-\!)(R_2\!-\!O\!-\!)(R_3\!-\!O\!-\!)P\!=\!O)$, d) trialkyl phosphines, $((R_1\!-\!O\!-\!)(R_2\!-\!O\!-\!)(R_3\!-\!O\!-\!)P)$, particularly trioctylphosphine (TOP), e) trialkyl phosphine oxides, $((R_1\!-\!)(R_2\!-\!)(R_3\!-\!)P\!=\!O)$, particularly trioctylphosphine oxide (TOPO).

The formulae listed above are only pseudo-structural formulae. The individual oxygen atoms (O) therein are all bound to the phosphorus atom (P). R1, R2, R3 are at first selected from branched or unbranched alkane chains comprising at least one carbon atom or they are selected from the comprising phenyl, tolyl, xylyl, or benzyl.

In particular, the esters named under a) to c) form a bond, probably via the oxygen atom that is bound to the phosphorus with a double bond, which has a particularly suitable strength to bind to many of the metal starting compounds. This property of the bond is advantageous for the synthesis and allows to make exceptional nanoparticles of particular substance groups.

In particular, when the esters named under a) to c) are used, the metal salt particles show an even better solubility, a further improved dispersability and an even lower tendency to form agglomerates than when the other substances are employed for the controllion of particle growth.

The reason for this phenomenon lies probably in the partial degradation of the esters at a later time point during the synthesis, at which practically the total amount of metal starting compound and anion-donating starting material have already reacted to metal salt nanoparticles. Due to the partial degradation of the esters, products seem to be released at the same time which couple in a reactive manner to the surface of the particles that are already formed. This process leads to the above-named, further improved properties.

During this slow degradation process, alcohol groups of the esters named under a) to c) are probably eliminated. Apart from alcohol, a further degradation product formed by the reaction is phosphinic acid when an ester of phosphinic acid is used, phosphonic acid and a monoester of phosphonic acid when a diester of phosphonic acid is used, and a monoester or diester of phosphoric acid when a triester of phosphoric acid is used, respectively.

All of these degradation products (apart from the alcohols) contain acidic P—OH groups which are known to be able to form very strong bonds with metal ions. Thus the coupling of these degradation products onto the nanoparticles occurs possibly through binding to the metal ions of the particle surface.

Furthermore, it is conceivable that the alcohols liberated by the degradation process react with and couple to the particles. For phosphate-containing nanoparticles (such as lanthanum phosphate) for example, it is possible that the alcohol couples to a phosphate group of the particle surface by forming an ester bond.

Finally, it shall be mentioned that we exploit an analogous degradation of esters, that is the elimination of the alcohol groups, also with the esters named above as anion source. However, for this purpose esters are chosen which are thermally unstable, i.e. which release all of the alcohol groups fast and completely already during the first stages of the synthesis process. The in this case complete elimination of all alcohol groups leads to the anion which then reacts with the metal starting compound.

Mixtures of organophosphorous compounds can also be used in order to flexibly modify the synthesis for the preparation of nanoparticles out of different substance groups.

It is possible to achieve a further flexibility by adapting the synthesis to different substance classes. The mixture that is then used consists of at least one of the above-named growth-controlling substances and one or more solvents, where the metal-chelating properties of these solvents are weaker than those of the growth-controlling components. Preferred are such solvents as are able to release at least partially some water of crystallization of the metal starting compounds. The use of such a mixture may also be of advantage for another reason, as discussed in the following paragraph:

For example, according to an individual aspect of the present invention, trialkyl phosphates and trialkyl phosphines are employed as coordinating solvent. This implies the use of relatively large amounts of these substances; e.g. 6 l of tris(ethylhexyl) phosphate per 1 mol of metal ions (Ce, Tb, and La together) are used accordingly for the synthesis of $LaPO_4$:Ce,Tb nanoparticles, for example:

300 ml of tris(ethylhexyl) phosphate+20 mmol of cerium chloride+22.5 mmol of lanthanum chloride+7.5 mmol of terbium chloride. This corresponds to a molar ratio of tris(ethylhexyl) phosphate to metal of approximately 13:1. Depending on the choice of the trialkyl phosphate and the trialkyl phosphine, respectively, and particularly on the length of the alkyl residue or the nature of the functional groups of the alkyl residues, the use of such large amounts may be inconvenient.

This happens, for example, if the precipitation of the nanoparticles succeeds only incompletely achieved or only by using very large amounts of solvents, or if the substances are very expensive or their synthesis is laborious. The latter occurs especially when functionalized trialkyl phosphates and trialkyl phosphines are used.

Therefore, if, according to the present invention more preferably a trialkyl phosphate or a trialkyl phosphine is used as regulating component during the formation of nanoparticles, and if for each mol of metal ions less than 10 mol, preferred 0.9 to 5 mol, and more preferred 0.95 to 1.5 mol, of the controlling component are used, then it is possible to simplify the synthesis and to make it cheaper because small quantities of the growth controlling components are employed. These ranges of molar quantities universally apply to all of the disclosed substance classes of nanoparticles.

In these cases mixtures of solvents may be used which contain, as explained, only a relatively small proportion of trialkyl phosphate and triallyl phosphine, respectively; the bottom limit being somewhat less than one mol of trialkyl phosphate and trialkyl phosphine, respectively, for each mol of metal ion (i.e. 1:1 according to the nomenclature given above).

According to the present invention, the other components of the solvent mixture are preferably chosen in a way that the boiling point of the mixture lies at a temperature which is sufficiently high to allow the formation of nanocrystals. This temperature is called herein synthesis minimum temperature. The amount of the other comments is then high enough allowing the synthesis mixture to keep the nanoparticles that are formed during the synthesis reaction in solution.

Preferred are then such components which degrade during the reaction process as little as possible.

More preferred are components which allow, after the end of the reaction, to be removed by distillation at reduced pressure without degradation. The distillation should be a simple method as usually employed in the laboratory, e.g. using an oil pump for the vacuum, not better than 0.01 mbar, and a water bath or oil bath providing a distillation temperature not greater than 200° C., which corresponds to approx. 480 Kelvin.

Further, it is preferably possible to add to the synthesis mixture at least one further, preferably metal-chelating component, preferably in order to displace any water of crystallization present in the metal salt starting compounds. This is in particular a) an ether compound, preferred dipentyl ether, dihexyl ether, diheptyl ether, dioctyl ether, dibenzyl ether, diisoamyl ether, ethylene glycol dibutyl ether, diethylene glycol dibutyl ether, or diphenyl ether, or/and b) an alkane compound that boils above the synthesis minimum temperature, preferred dodecane or hexadecane (not metal-chelating), for example to dilute the reaction mixture, or/and c) an amine compound, preferred dihexylamine, bis(2-ethylhexyl)amine, trioctylamine, tris(2-ethylhexyl)amine.

If, further advantageously, R1, R2, or R3 are branched or unbranched alkane chains that carry at least one of the following groups:

carboxyl group (—COOH), carboxylic acid ester group (—COOR), amino groups (—$NH_2$) and (—NHR), hydroxyl group (—OH), cyano group (—CN), mercapto group (—SH), bromine (—Br) and chlorine (—Cl), or a combination of these groups, then the growth controlling components can very flexibly be functionalized. This is the reason why it is possible to specifically synthesize nanoparticles of many different substance classes (phosphates, halophosphates, arsenates, . . . ) as mentioned at the beginning. Nevertheless, the synthesis is relatively inexpensive because quite small amounts of the expensive controlling compounds are being used.

The starting material used as cation source is preferably a chloride, e.g. $LaCl_3$, for preparing lanthanum phosphate nanoparticles, or bromides, iodides, alkoxides, or acetylacetonate.

In addition to the basic steps (see above), a further, preferred development of the synthesis method of the present invention may contain the following additional steps:

a) preparation of a first solution of the cation starting material in a—preferably lower—alcohol, particularly methanol, wherein preferably a metal salt is used that is non-oxidative and soluble in the synthesis mixture, and b) mixing of the first solution with the already prepared solvent, comprising at least one component controlling the crystal growth of the nanoparticles, for example a phosphorganic compound, in order to prepare the metal-chelating synthesis mixture, c) keeping the synthesis mixture heated under inert gas, in particular under nitrogen, from which the alcohol is removed by distillation preferably before or during the synthesis.

In case the nanoparticles shall be isolated after completion of the synthesis reaction, the method according to the present invention includes some further optional steps for a subsequent treatment:

a) removing of one or more of the solvent components from the synthesis mixture by distillation, preferred under vacuum, preferred only after the end of the synthesis period, or/and b) purification of the nanoparticles by washing with an alcohol, preferred with ethanol, or by diafiltration to get rid of any attached by-products.

Depending on the acid content of the synthesis mixture and the nature of the starting materials that are used, the method of the present invention in all its variations can contain the further step to more or less, as required, neutralize the synthesis mixture using a base that is soluble in the synthesis mixture, preferred trihexylamine, triheptylamine, trioctylamine, or tris(2-ethylhexyl)amine.

Hydrated metal salts are preferably being used as starting material because they are often better soluble. Moreover, the release of small amounts of water during the reaction accelerates the degradation of certain anion-donating starting compounds such as alkoxides and esters, and thereby increases the reaction rate.

Further, several different metal salts can also be employed for the preparation of doped nanoparticles, where at least one of the metals is used as doping agent for the nanoparticles that are being made.

The spectrum of synthesis variations according to the present invention allows a very broad field of application, depending on the choice of the starting materials and the other components of the synthesis mixture. The method is also suitable for synthesizing semiconductor nanoparticles, in particular of III-V- or of II-V-semiconductors.

Through specific usage of the solvent components of the present invention—e.g. the trialkyl phosphates as controlling component for the growth—it is now for the first time possible to prepare nanoparticles of the following substance groups that are characterized, as compared to the hydrothermal synthesis, by a narrow size distribution with a small maximum size and that are concomitantly synthesized at a high yield rendering a subsequent size selection superfluous:

These are the phosphates of rare earth metals, of IIIrd subgroup elements and of calcium (Ca), strontium (Sr), barium (Ba), characterized by an upper limit of the particle size of about 15 nm, preferably of 10 nm. It is only possible to prepare the nanoparticles in such a narrow distribution and at such small sizes because of the very low tendency of the particles to agglomerate, i.e. to grow together with each other. This advantageous effect is made possible by the use for example of the above-named trialkyl phosphates during the synthesis.

The following section relates to the synthesis method for and the application of nanoparticles capable of fluorescence. In particular, it relates to aspects of the doping.

The nanoparticle substance obtained by the synthesis method may contain particles capable of fluorescence which do not much 'age', i.e. have a long-term stability concerning their property to glow, and which are more resistant against heat and other environmental influences than the substances based on organic fluorescent dyes.

This aspect is essentially based on the following idea: a separate, complete, inorganic nanoparticle is prepared that glows by itself after a suitable energetic excitation by a suitable kind of energy supply, particularly by electromagnetic radiation at an appropriate frequency, for example of the infrared (IR), the visible (VIS) or the ultraviolet (UV) region, or by X-rays and, if necessary, by particle or electron radiation, respectively. When incorporated into a stabile host material, for example a host lattice, the properties to glow are quite stable, even in case of complicated physical parameters of the environment, such as an increase in pressure, temperature, or their fluctuation cycles, and even in case of a chemical environment that exerts an anti-fluorescence effect, of photooxidation, acidic or alkaline environment, of organic solvents, etc.

This central advantage of the substances according to the present invention in comparison with commercial organic fluorescent dyes and fluorescent markers is due to the inorganic nature of the nanoparticles. These nanoparticles therefore are ready to be used at exposed positions for many application fields.

It is within the scope of the present invention to develop at least the following subject matters which are claimed herein:

a preferred preparation method for nanoparticles of many different substance groups, in particular for inorganically doped nanoparticles, and the immediately resulting product thereof;

a generic describable lot of substances, in the sense of products, no matter in which physical form they are present, e.g. as powder concentrate, colloid, or aerosol;

a nanoparticle carrier substance—in the following text abbreviated as NPCS—which carries nanoparticles of the present invention, for example in a three-dimensionally homogenous or inhomogenous arrangement, such that an incorporation into the carrier substance in the sense of an embedment or more of a coating with it is achieved;

any objects to which the carrier substance and/or the doped nanoparticles are deliberately attached, for example for the purpose of a particular marking;

different ways of use and possibilities of application for the substances of the invention and generally for nanoparticles of the family of phosphors, for doped nanoparticles; as well as any detection methods for the recognition (in the sense of a proof) of the fluorescence of a test substance as being identical with a predetermined nanoparticle type of the invention that shows a main peak in the fluorescence emission; as well as the corresponding detection device.

For the above-named subject matters, the independent claims are referred to.

The subclaims describe advantageous developments and improvements of the respective subject matters pertaining to the invention.

According to the present invention, the inorganic nanoparticles capable of fluorescence are prepared by a liquid phase synthesis using an organic solvent. First, this gives colloidal solutions of highly crystalline nanoparticles. By using further steps of the preparation method, these nanoparticles in solution can then be precipitated and dried. According to the solvent that is used, the cation source or anion source for the host lattice that are used and, if necessary, whether one or some further cation sources (preferred are metal salts) as doping agent are applied, this then results in desired nanoparticles and in particular properties of the nanoparticles.

In another aspect of the present invention, a synthesis method for inorganically doped nanoparticles capable of fluorescence is disclosed, wherein the nanoparticles of the final product are incorporated in a host material, comprising at least one dopant, and wherein an organic solvent, preferably as already described above, is used for a liquid phase synthesis of the nanoparticles. The host material is particularly a host lattice that comprises compounds of the type XY, wherein X is a cation of one or more elements of the main groups 1a, 2a, 3a, 4a, the subgroups 2b, 3b, 4b, 5b, 6b, 7b, or of the lanthanides of the periodical system, and wherein Y is either a polyatomic anion of one or more of the elements of the main groups 3a, 4a, 5a, of the subgroups 3b, 4b, 5b, 6b, 7b, and/or 8b as well as of elements of the main groups 6a, and/or 7, or a monoatomic anion of the main groups 5a, 6a, or 7a of the periodical system.

The final product of the method of the invention and of modifications of the method is in each case a substance, i.e. a chemical substance, for which an absolute substance protection that is independent of the preparation method is claimed herein.

A host material can preferably include compounds of the group consisting of sulphides, selenides, sulphoselenides, oxysulphides, borates, aluminates, gallates, silicates, germanates, phosphates, halophosphates, oxides, arsenates, vanadates, niobates, tantalates, sulphates, tungstates, molybdates, alkalihalogenates as well as other halides, or nitrides.

Further, in the first aspect of the present invention as mentioned above, one ore more elements selected from a group comprising elements of the main groups 1a, 2a, or Al, Cr, Tl, Mn, Ag, Cu, As, Nb, Ni, Ti, In, Sb, Ga, Si, Pb, Bi, Zn, Co, and elements of the lanthanides are used for the doping.

Preferably, an appropriate pair of dopants, if necessary for each of the desired fluorescence colours, that have a good energy transfer can be used, in particular cerium and terbium, wherein one of the dopants is characterized as energy absorber, in particular as UV-light absorber, and the other as fluorescence light emitter.

As a matter of principle, any of the following compounds can be chosen as a material for the doped nanoparticles. In the notation below, the host compound is given on the left of the colon and one or more doping elements are given on the right of the colon. When chemical elements are separated by commas and are put in brackets, they can be used at choice. A first list is defined as follows, from which, depending on the desired fluorescence property of the nanoparticles that are to be prepared, one or also more of the compounds presented in the list can be chosen:

LiI:Eu; NaI:Tl; CsI:Tl; CsI:Na; LiF:Mg; LiF:Mg,Ti, LiF:Mg,Na; $KMgF_3$:Mn; $Al_2O_3$:Eu; BaFCl:Eu; BaFCl:Sm; BaFBr:Eu; $BaFCl_{0.5}Br_{0.5}$:Sm; $BaY_2F_8$:A (A=Pr, Tm, Er, Ce); $BaSi_2O_5$:Pb; $BaMg_2Al_{16}O_{27}$:Eu; $BaMgAl_{14}O_{23}$:Eu; $BaMgAl_{10}O_{17}$:Eu; ($BaMgAl_2O_4$:Eu); $Ba_2P_2O_7$:Ti; (Ba, Zn, Mg)$_3Si_2O_7$:Pb; Ce(Mg, Ba)$Al_{11}O_{19}$; $Ce_{0.65}Tb_{0.35}MgAl_{11}O_{19}$; $MgAl_{11}O_{19}$:Ce,Tb; $MgF_2$:Mn; MgS:Eu; MgS:Ce; MgS:Sm; MgS(Sm, Ce); (Mg, Ca)S:Eu; $MgSiO_3$:Mn; $3.5MgO0.5MgF_2GeO_2$:Mn; $MgWO_4$: Sm; $MgWO_4$:Pb; $6MgOAs_2O_5$:Mn; (Zn, Mg)$F_2$:Mn; (Zn, Be)$SO_4$:Mn; $Zn_2SiO_4$:Mn; $Zn_2SiO_4$:Mn,As; ZnO:Zn; ZnO:Zn,Si,Ga; $Zn_3(PO_4)_2$:Mn; ZnS:A (A=Ag, Al, Cu); (Zn, Cd)S:A (A=Cu, Al, Ag, Ni); $CdBO_4$:Mn; $CaF_2$:Dy; CaS:A (A=lanthanides, Bi); (Ca, Sr)S:Bi; $CaWO_4$:Pb; $CaWO_4$:Sm; $CaSO_4$:A (A=Mn, lanthanides); $3Ca_3(PO_4)_2Ca(F, Cl)_2$:Sb, Mn; $CaSiO_3$:Mn, Pb; $Ca_2Al_2Si_2O_7$:Ce; (Ca, Mg)$SiO_3$:Ce; (Ca, Mg)$SiO_3$:Ti; $2SrO6(B_2O_3)SrF_2$:Eu; $3Sr_3(PO_4)_2.CaCl_2$:Eu; $A_3(PO_4)_2.ACl_2$:Eu (A=Sr, Ca, Ba); (Sr,Mg)$_2P_2O_7$:Eu; (Sr, Mg)$_3(PO_4)_2$:Sn; SrS:Ce; SrS:Sm,Ce; SrS:Sm; SrS:Eu; SrS:Eu,Sm; SrS:Cu,Ag; $Sr_2P_2O_7$:Sn; $Sr_2P_2O_7$:Eu; $Sr_4Al_{14}O_{25}$:Eu; $SrGa_2S_4$:A (A=lanthanides, Pb); $SrGa_2S_4$:Pb; $Sr_3Gd_2Si_6O_{18}$:Pb,Mn; $YF_3$:Yb,Er; $YF_3$:Ln (Ln=lanthanides); $YLiF_4$:Ln (Ln=lanthanides); $Y_3Al_5O_{12}$:Ln (Ln=lanthanides); $YAl_3(BO_4)_3$:Nd,Yb; (Y,Ga)$BO_3$:Eu; (Y,Gd)$BO_3$:Eu; $Y_2Al_3Ga_2O_{12}$:Tb; $Y_2SiO_5$:Ln (Ln=lanthanides); $Y_2O_3$:Ln (Ln=lanthanides); $Y_2O_2S$:Ln (Ln=lanthanides); $YVO_4$:A (A=lanthanides, In); Y(P,V)$O_4$:Eu; $YTaO_4$:Nb; $YAlO_3$:A (A=Pr, Tm, Er, Ce); YOCl:Yb,Er; $LnPO_4$:Ce,Tb (Ln=lanthanides or mixtures of lanthanides); $LuVO_4$:Eu; $GdVO_4$:Eu; $Gd_2O_2S$:Tb; $GdMgB_5O_{10}$:Ce,Tb; LaOBr:Tb; $La_2O_2S$:Tb; $LaF_3$:Nd,Ce; $BaYb_2F_8$:Eu; $NaYF_4$:Yb,Er; $NaGdF_4$:Yb,Er; $NaLaF_4$:Yb,Er; $LaF_3$:Yb,Er,Tm; $BaYF_5$:Yb,Er; $Ga_2O_3$:Dy; GaN:A (A=Pr, Eu, Er, Tm); $Bi_4Ge_3O_{12}$; $LiNbO_3$:Nd,Yb; $LiNbO_3$:Er; $LiCaAlF_6$:Ce; $LiSrAlF_6$:Ce; $LiLuF_4$:A (A=Pr, Tm, Er, Ce); $Gd_3Ga_5O_{12}$:Tb; $Gd_3Ga_5O_{12}$:Eu; $Li_2B_4O_7$:Mn; $SiO_x$:Er,Al (0<x<2).

A second list from which compounds are to be selected is defined as follows:

$YVO_4$:Eu; $YVO_4$:Sm; $YVO_4$:Dy; $LaPO_4$:Eu; $LaPO_4$:Ce; $LaPO_4$:Ce,Tb; ZnS:Tb; $ZnS:TbF_3$; ZnS:Eu; $ZnS:EuF_3$; $Y_2O_3$:Eu; $Y_2O_2S$:Eu; $Y_2SiO_5$:Eu; $SiO_2$:Dy; $SiO_2$:Al; $Y_2O_3$:Tb; CdS:Mn; ZnS:Tb; ZnS:Ag; ZnS:Cu; $Ca_3(PO_4)_2$:$Eu^{2+}$; $Ca_3(PO_4)_2$:$Eu^{2+}$, $Mn^{2+}$; $Sr_2SiO_4$:$Eu^{2+}$; or $BaAl_2O4$:$EU^{2+}$.

A third list from which doped nanoparticles are to be selected is defined as follows:

$MgF_2$:Mn; ZnS:Mn; ZnS:Ag; ZnS:Cu; $CaSiO_3$:A; CaS:A; CaO:A; ZnS:A; $Y_2O_3$:A; or $MgF_2$:A, wherein A is an element of the lanthanides.

An another aspect of the present invention is characterized by the fact that metal chlorides are used for the synthesis method of the invention to obtain the cationic component of the host material, or a phosphate salt is used to obtain its anionic component, and a chemical capable to neutralize acids, preferred an amine, more preferred trioctylamine ($C_{24}H_{51}N$), is added to the synthesis mixture. When chloride salts are being used instead of the prior art nitrate salts, the yield of the material can be increased with respect to the amount of the employed metal salts by more than 70% to approx. 80% making a production method at industrial scale possible.

This method allows advantageously the preparation of a host material, comprising a metal cation and phosphorus as component of the anionic part of the host lattice.

Apart from the above-named phosphororganic compounds, esters of phosphinic acid, diesters of phosphonic acid, triesters of phosphoric acid (trialkyl phosphates), that are included as growth controlling component, the following chemical substances can be used in the above-named aspect of the present invention preferably as solvent or as a component of the solvent for the synthesis of the nanoparticles of the present invention:

phosphoric amide, preferred hexamethyl phosphoric triamide, phosphoric amide oxide, preferred tris-(dimethylamino)-phosphine oxide, tris(ethylhexyl) phosphate, trialkyl phosphine, particularly preferred trioctylphosphine (abbreviated: TOP), and preferred trioctylphosphine oxide (abbreviated: TOPO), both of which are commercially available from the company Sigma Aldrich Chemie GmbH, Deisenhofen, Germany, and phosphoric amide, preferred tris-(dimethylamino)-phosphine, phosphoric amide oxide, preferred tris-(dimethylamino)-phosphine oxide.

The already mentioned, preferred solvents can be used advantageously to obtain $LaPO_4$ as particularly preferred host material. A $LaPO_4$ host lattice can be doped preferably in such a way that two elements in relatively to each other different concentrations are used for the doping, wherein one of the doping elements has a local maximum in the absorption spectrum for light, preferred for UV-light, and the other doping element has a fluorescence emission spectrum with at least one local maximum that has a distance $\Delta\lambda/\lambda$ from the absorption maximum of the first doping element of at least 4%, preferred of more than 20%.

This procedure shall guarantee that the doped nanoparticles are excited by invisible light and emit the fluorescence in the visible range of the light. Thus the excitation light does not interfere with the emitted fluorescence. Such a procedure is recommended particularly in the field of security markings which shall be dealt with in more detail below. By a clever choice of the dopants it is possible to select a very special excitation spectral range, for example in the UV-C region of around 250 nm.

The method improved by the usage of TOP/TOPO (see above) as solvent can be applied to obtain the more preferred $LaPO_4$ as host material. $LaPO_4$ is doped using a first, absorbing dopant which plays the role of a sensitizer, most preferred $Ce^{3+}$ as selective UV-C absorber, and a second, emitting doping material, most preferred $Tb^{3+}$.

If TOP and/or TOPO is used as solvent, and if a doping with terbium is achieved in the range from 0.5 to 30 mol percent, preferred from 5 to 25 mol percent, and most preferred from 13 to 17 mol percent, wherein the respective molar ratio between lanthanum and cerium is a ratio ranging from 0.13 to 7.5, preferred from 0.25 to 4, and most preferred from 0.9 to 1.1, and if metal chloride salts serve as metal source, then high-quality fluorescent nanoparticles can be prepared. In particular, these nanoparticles can advantageously be applied to the field of increased security marking.

In comparison to phosphate esters, TOP and/or TOPO have some advantages when used as solvent during the preparation method. These are a higher synthesis temperature ranging from approx. 530 to approx. 620 Kelvin, then, associated with this, an improved incorporation of the doping agent and, as a result, an increased intensity of the emitted light which is a crucial factor for the applicability of a fluorescence marker. In addition, high synthesis temperatures allow a successful doping also of a host lattice even if the atomic size of the dopants matches only badly the ionic size of the host ions. Thus, diverse fluorescent dyes can specifically be made.

Immediately after the synthesis, the surface of the nanoparticles is coated by a layer consisting of residual solvent molecules of the growth controlling components, for example of trioctylphosphine (TOP) and trioctylphosphine oxide (TOPO), or of one of the others described above. This allows a simpler way to handle the nanoparticles after their synthesis, because these surface molecules (residual solvent molecules) cause an improved solubility in standard solvents without chemically modifying the particles in a second laborious step.

After precipitation and drying, for example by using hot air, the nanoparticle substance obtained with the method may be in the form of a softly pulverizable, very fine powder concentrate. This powder can then be embedded in a large number of carrier substances, depending on the requirements of the particular case of application. Thus nanoparticles may be integrated into films, for example into aluminium foils by impression rolling, or into polymer films, e.g. made of polyethylene or polypropylene, etc., by addition to the liquid polymer phase.

The substance according to the present invention is an inorganic compound and therefore resistant against fading. Thus even under extreme conditions such as temperatures of near 0 (zero) Kelvin to approx. 400 Kelvin, it can be used with high efficiency, without being finished in composition with another protective material, as well as in organic and aqueous solvents.

In contrast to organic fluorescence markers, there is no concentration quenching at high particle concentrations.

The material may be adapted to the solution conditions in different solvents by subsequent chemical modification of the surface.

The nanoparticle substance obtained with the method can further exist as colloid in a carrier liquid, in particular in a varnish or in a paint liquid, or as dust-like powder/aerosol in a carrier aerosol or gas.

The absolute central point of the present invention concerning the application is the nature of the emitted light of the nanoparticles prepared according to the invention. The emission lines, that is the distribution of the wavelengths of the emitted light of the above-described doping atoms chosen from the rare earth elements, are very sharp and they are lying, in contrast to the excitation light, within the visible range of the spectrum.

This results in a characteristic property of the particular nanoparticle type which arises from the specific colour and the specific widths at half-height of the emitted light of one or several specifically chosen emission dopant(s). At the time being, no other material than the claimed rare earth element-doped substances reaches these properties. The fact that the choice of the absorption dopant can be made specifically, as mentioned above with the preferred element cerium, adds to the originality in the sense of a distinctiveness against other fluorescent substances. This fact can be exploited advantageously for increased security markings.

In yet another aspect of the present invention, the compounds known as so-called phosphors (see 'Ullmanns Encyclopedia of Industrial Chemistry, WILEY—VCH, 6th Edition, 1999, Electronic Release, Luminescent Materials: 1 Inorganic Phosphors') may now be prepared not only as prior art macromaterial—also called bulk material—but also as nanoparticles using a simple (no requirement for an autoclave) and thus economical method.

Basically, the necessary and specific steps of the method for the doping of nanoparticles are then omitted. For the remaining parts of the method—synthesis in organic solvents from the starting materials as they are described above—it therefore can be referred to the description of the preparation method for inorganically doped nanoparticles.

This leads to a new way for using this set of substances—called phosphors above—as nanoparticles, in particular for the marking of objects, and, to be precise, this is possible with or without an independent doping.

In this aspect of the invention, size ranges of the nanoparticles can specifically be produced from 1 nm to around 1000 nm, in particular when oxygen or water or steam are excluded during the synthesis process. According to the invention, this results in a narrow size distribution as explained below in more detail.

Depending on which of the controlling components of the solvent are used, a very uniform size of the nanoparticles may be obtained. Even homogeneously small nanoparticles may be prepared according to the present invention that lie within a size range of 1 to 8 nm, preferred within a medium range of 4 to 5 nm with a standard deviation of less than 30%, preferred of less than approx. 10%. This allows the integration of the nanoparticles into very finely structured carrier materials without causing any noticeable alteration in the carrier structure, just as required by the particular application purpose, e.g. by the incorporation into very thin and/or very soft polymer films. For example films stay transparent and do not become clouded as would be the case using larger (larger than approx. 50 nm) particles.

This applies in particular to the nanoparticles of the substance group including phosphates of rare earth metals, or phosphates of IIIrd main group elements, or phosphates of calcium (Ca), strontium (Sr), or barium (Ba), wherein these nanoparticles have a size, measured along their longest axis, of maximally 15 nm, preferred of maximally 10 nm, and most preferred of 4 to 5 nm with a standard deviation of less than 30%, preferred of less than 10%.

The above-mentioned possibility to prepare nanoparticles of the family of phosphors leads according to the invention in particular to the use of phosphors, particularly of phosphate-containing nanoparticles, and preferred to the use of doped nanoparticles, and more preferred to the use of the above-described inorganically doped nanoparticles as fluorescence marker in general. These fluorescence markers can label any objects, particularly carriers for information such as compact discs, computer components, automobile components, motor elements, documents, locking devices, anti-burglary devices, objects transparent to visible light, e.g. windows, glasses, contact lenses, or transparent screens, and in particular in the field of increased security marking such as required or desired for banknotes, cheques, and cheque cards, as well as for works of art and jewellery.

Through incorporation of the above-named groups of nanoparticles or of nanoparticle carrier substances carrying them, into objects that are to be marked, be it by coating or by covering with a film, or by applying of a varnish, any objects can be marked according to the invention. Depending on the requirements of each case, this labelling process can be optimised to be convenient for the preparation procedure. In addition, the external appearance of the object, its haptic properties or other object-related properties are not disturbed by the label.

Preferably, the nanoparticles are incorporated into or attached to the object that is to be marked in such a way that the particles of the invention or the substance of the invention is excitable by an energy source that has been determined in advance, preferred by electromagnetic irradiation, in particular radiation with a wavelength below 300 nm, or by irradiation by particles or electrons. The excitation then causes a fluorescence emission, preferred in the visible range of light, or in the UV- or near IR-range (NIR), that is detectable externally to the object.

The method allows, in principle, to choose one ore more nanoparticle types so that the special requests demanded from the marking are granted. In particular, one or more of the excitation spectral ranges can be deliberately be selected according to their position within the spectrum and their line width. Similarly, the fluorescence spectrum can specifically be chosen to be of one colour, multi-coloured, visible (VIS), or to be invisible and only detectable with the help of specific tools, etc.

In addition, it is possible to mark liquids and gases for the purpose to test whether or not such a substance is somewhere present, if the NPCS is incorporated into the respective medium. This may be relevant for security checks, such as testing for tears on aeroplanes, pipelines, water-pipes and other liquid-carrying systems. The advantage lies in the special, distinctive properties of the material which allows to easily trace the test medium.

The material is completely transparent, scatter-free and colourless and thus can be applied everywhere without being recognized.

Also when products are returned by the customer to the manufacturer, a definite label by the manufacturer is necessary in connection with the return procedure. A labelling is recommended that is not visible for the normal eye but only after the excitation by special energy forms, such as UV-C light with a wavelength of, for example, 250 nm.

In the field of increased security marking, it is only possible to excite the material, if desired and prepared accordingly, to fluoresce, for example in the case of a cerium/terbium doping of $LaPO_4$, by using a special UV-C lamp of 255 nm wavelength in order to make the corresponding marking visible. So-called black light lamps which emit light at 366 nm, are not suitable for this excitation.

Such a way of use may be allowed for example by incorporation of the marking substance into a transparent material, i.e. into a material that is 'open' in the spectral range of the excitation, preferred into a polymer that is open in the UV-C range (wavelength<300 nm) as is the case with for example commercial polypropylene or polyethylene etc. Equally, metal foils can be used as long as they fulfil this condition. The thinner the foil, the less important becomes this criterion, since in extremely thin foils, the incorporated nanoparticles lie very near to the surface so that there practically always can occur some excitation.

The wavelengths of excitation and emission are separated advantageously by up to 400 nm when a suitable pair of dopants is used. This allows an unmistakable detection of the emission wavelength without any interference of the excitation light. For this application, an excitation in the UV-C range of about 255 nm or in the infrared range is preferred since they lie both outside the visible light range and are relatively simple to handle.

It is also possible to tag printed matter, such as paper, acetates, etc., with the nanoparticles of the invention, for example by using an appropriate pattern and spraying a carrier liquid. The nanoparticles stay invisible until just after the excitation when they colourfully or multi-colouredly show the corresponding pattern, images, etc.

In the field of optoelectronics, even photo cells and other light-sensitive components can be coated with the substance of the invention, since the fluorescence appears only in a spectral range outside of the operation range of the component and does therefore not interfere with the regular operation.

In order to facilitate the proof of authentication for a marking and to prevent that it needs to be performed by a manual, laborious spectroscopic analysis method, the following detection method that may advantageously be automated is proposed according to the present invention. This method has the purpose to test rapidly and simply whether or not a certain sample or test substance has been marked with a predetermined nanoparticle type:

The detection method of the invention to recognize the fluorescence of a test substance as identical with a predetermined nanoparticle type (reference substance) needs in its simplest version a fluorescence emission main peak which corresponds to that of the emitting dopant being characteristic for the nanoparticle type. The principle of detection consists basically of the application of up to three interference filters which are specifically open for a certain wavelength. Since the emission light is a decidedly narrow band, the detection is made by a comparison measurement within a narrow distance of this band. If the apparatus detects approx. 1–10 nm on the left and on the right of the emission main line more than 10–50%, preferred more than 5–20% of the intensity of the main line, then the test substance is a counterfeit product. This simple version of the method comprises then the following, fundamental steps:

exciting the substance using an excitation spectrum that is known to be suitable for the predetermined nanoparticle type, as already mentioned further above, filtering the spectral region of the main peak, for example using a suitably prepared interference filter, filtering next to the main peak at least one secondary spectral region where only a low intensity is expected for the predetermined nanoparticle type, for example likewise by using an appropriately adjusted interference filter, quantifying the filtered emission intensities within the predetermined spectral regions, for example by using a multitude of photosensitive elements, e.g. photo cells, of which each one is coupled directly by optical means to a particular interference filter, and determining the relation of the filtered emission intensities to each other, for example by analysing the signal coming from the photo cell, admitting that a test substance is identical with the predetermined nanoparticle type, if one or several of the relations of secondary spectral region emission to main peak emission is (are) below an appropriate, predetermined threshold value.

Since the width at half-height of a main peak of the reference substance is known beforehand and thus defined, it can be used advantageously to define the sharpness of the reference peak and to decide on the above-mentioned threshold value as requirement for authentication.

If the secondary region is recorded only at one side of the main peak, there is one threshold value; in general there are two threshold values, when the measurement of the secondary region is made at both sides of the main peak. In case the peak is sufficiently symmetrical, one threshold value may be enough.

Advantageously, two or more secondary spectral regions are filtered and evaluated apart from the main peak. This can lead to an increased security of the detection.

The advantage of the two versions just described is that time and expense to measure and analyse the signals are only minimal because the signal coming from the photo cell is easily and inexpensively digitalized and analysed by computer.

In another version of the detection method of the invention, a, if necessary already existing, special image, such as barcodes or more complex figures, or pattern of the fluorescence source is additionally recorded, for example by using a CCD camera, and analysed by using an appropriate prior art image processing logic. This allows an increase in the demands on security against counterfeit in the field of increased security markings because in addition to the spectral identity, the pattern also has to match the reference pattern that is saved separately. Only then the method admits the marking of the test substance as being authentic with that of the reference substance.

The detection device in accordance with the method is in its structure essentially based upon the functional features as they are described above. It is also possible to manufacture portable detectors because all of the elements of the detection system are small and easy to produce and, except for the programming logic for analysing the signal, are commercially available.

Aside from the above-mentioned possibility of application for the purpose of marking, the substances of the invention can be used as protection layer against hard UV radiation and as a converter of it into visible light, as long as they take up energy in the hard UV range and emit it in the visible range of the spectrum. Thus it is possible to clearly enhance the sensitivity of commercial detectors within this energy spectrum.

When used in combination with solar-energy collectors—for example, when the light-absorbing surface possesses a coating of the invention displaying the converter properties mentioned above—it is possible to convert hard UV radiation into visible light and thus contribute to an enhancement of the efficiency of the collector.

DRAWINGS

Embodiments of the invention are illustrated in the figures and are further explained in the description that follows.

DETAILED DESCRIPTION OF THE EMBODIMENTS

Figure 1:
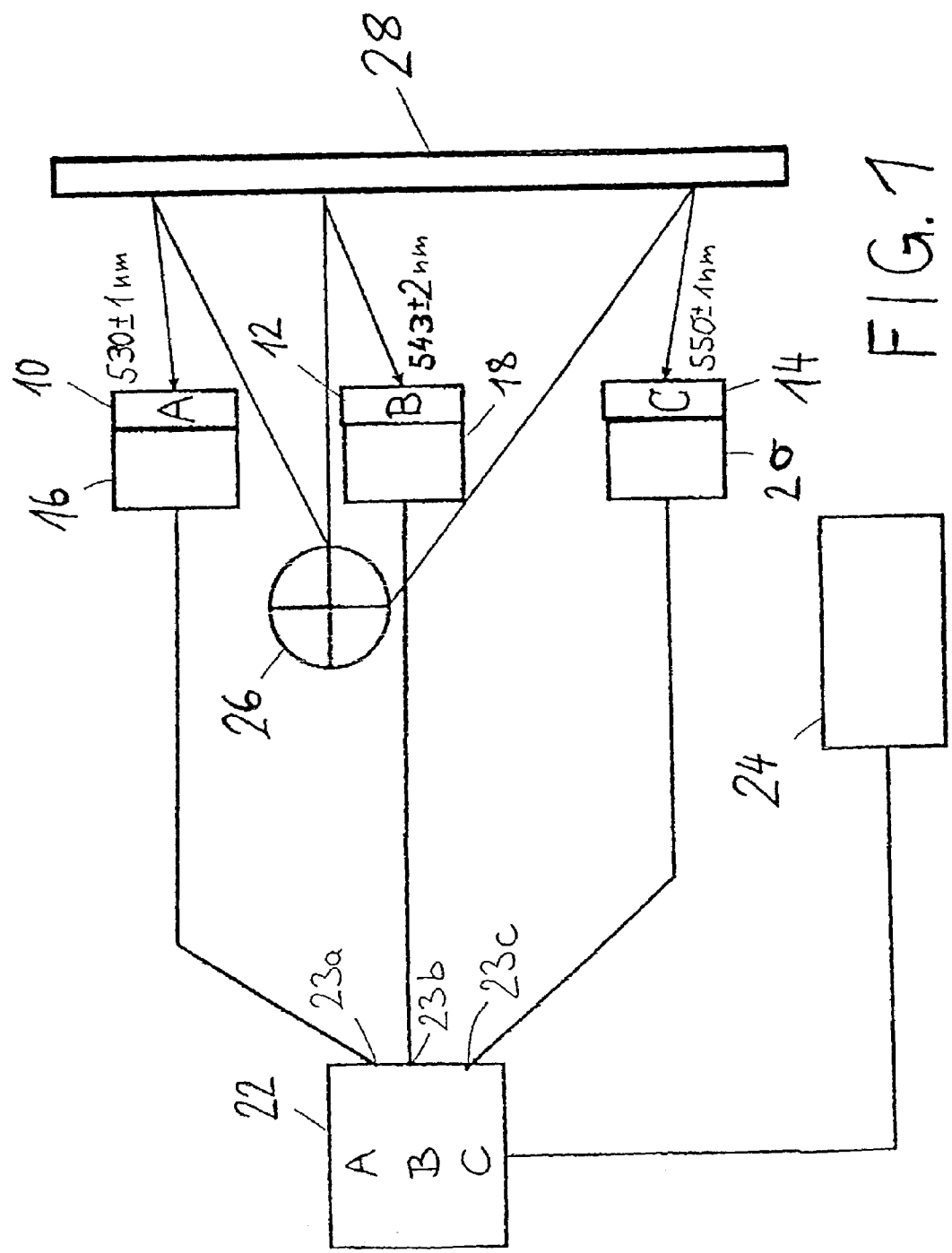
FIG. 1 is a schematic illustration of a circuit diagram showing an embodiment according to the invention of a detector device in a simpler form.

The following paragraph gives first a detailed description of a preferred embodiment for a synthesis method of the invention. The example is the preparation of $LaPO_4Ce:Dy$.

1. $LaPO_4Ce:Dy$ a) Into a first, 50 ml-containing round-bottom flask with reflux condenser, temperature sensor and heating mantle attached 20 ml of commercially available TOP (90%) are poured and evacuated at approx. 323 Kelvin (K) for one hour with stirring.

b) In a second flask 2 g of TOPO and 2.3 ml of TOP are mixed and slightly heated until the TOPO is melted and the mixture is homogenous.

c) In a third flask the salts $LaCl_3$ (0.001 mol), $CeCl_3$ (0.0012 mol), and $DyCl_3$ (0.00024 mol) are dissolved in 3 ml of methanol and subsequently poured into the TOP/TOPO mixture.

d) Then 0.0028 mol of $H_3PO_4$ are added to the above-named 50 ml round-bottom flask and stirred under vacuum at 323 Kelvin.

e) After this, the methanol is removed from the salt-TOP/TOPO-methanol mixture by distillation under vacuum at room temperature. The remaining solution is poured into the first, round-bottom flask.

f) Subsequently, the temperature is increased to 533 Kelvin and the reaction mixture is stirred overnight. The resulting nanoparticles can then be dissolved in 30 ml of toluene and are precipitated using 20 ml of methanol.

A substance is formed which, for example, g) may be dried under a controlled stream of warm air, e.g. of 310 Kelvin, which results in the formation of a solid.

h) As an option the solid may be pulverized by pressure-controlled grating to give a fine, dust-like powder. This also gives a powder with a desired grain size.

The next paragraph gives a description of a preferred embodiment for a synthesis method of the invention. The example is the preparation of $LaPO_4Ce:Tb$.

2. $LaPO_4Ce:Tb$ a) Into a 50 ml round-bottom flask with reflux condenser, temperature sensor and heating mantle attached 20 ml of tris(ethylhexyl) phosphate are poured and evacuated at approx. 323 K for 1 h with stirring.

b) In a second flask 10 ml of tris(ethylhexyl) phosphate and 3.2 ml of trioctylamine are mixed and 0.0028 mol of $H_3PO_4$ is added.

c) In a third flask the salts $LaCl_3$ (0.001 mol), $CeCl_3$ (0.0012 mol) and $TbCl_3$ (0.00024 mol) are dissolved in 3 ml of methanol and subsequently poured into the round-bottom flask.

d) As soon as the metal salts are completely dissolved in methanol, the mixture is poured into the round-bottom flask and the methanol is removed by distillation at 323 K.

e) The phosphoric acid-containing solution is then added and the reaction mixture is stirred overnight at a temperature of 472 K. As soon as the internal temperature is decreased to 448 K, f) the reaction is stopped, and g) the resulting nanoparticles can be precipitated from the solution by adding a 4-fold excess amount of methanol (80 ml).

The following section gives further descriptions of the synthesis of a few exemplarily chosen substances of the invention. In addition to the descriptions given herein, the disclosures of the following publications may be consulted for gallates and aluminates, respectively:

"Synthesis of Rare Earth Gallium Garnets by the Glycothermal Method", by Inoue, M. et al., in Journal of the American Ceramic Society, Vol. 81 No. 5, pp 1173–1183;

"Synthesis of submicron spherical crystals of gadolinium garnets by the glycothermal method", by Inoue, M. et al., in Journal of Materials Science Letters 14 (1995), pp 1303–1305;

"Synthesis of Yttrium Aluminium Garnet by the Glycothermal Method", by Inoue, M. et al., in Communications of the American Society, Vol. 74, No. 6, pp 1452–1454; and "Reactions of rare earth acetates with aluminium isopropoxide in ethylene glycol: Synthesis of the garnet and monoclinic phases of rare earth aluminates", by Inoue, M. et al., in Journal of Materials Science 33 (1998), pp 5835–5841.

3. Synthesis of $Y_3Al_5O_{12}$:Eu Nanoparticles:

In an autoclave glass vessel 4.26 g (20.8 mmol) of aluminium isopropoxide, 4.15 g (11.875 mmol) of yttrium acetate.4 $H_2O$, and 250 mg (0.625 mmol) of europium acetate.4 $H_2O$ are mixed with 100 ml of 1,6-hexanediol. The glass vessel is placed in an autoclave and loosely capped with a glass cap. To allow heat transfer to the vessel, the space between the inner wall of the autoclave and the glass vessel is filled with 50 ml of 1,6-hexanediol. Subsequently, the autoclave is closed, carefully evacuated twice and filled each time with nitrogen or argon (or another inert gas). Finally the autoclave is heated to 573 K and kept at this temperature for 4 hours. The autoclave is left to cool down. After the pressure is back to normal, the autoclave is opened. The content of the glass vessel is dissolved in 100–250 ml of isopropanol. The precipitate is collected by centrifugation and washed several times in isopropanol. Subsequently, it is washed with distilled water until peptization starts (=small particles of the precipitate dissolve again). The colloidal solution is centrifuged at 12,000×g for 60 min and the precipitate of the $Y_3Al_5O_{12}$:Eu nanoparticles is separated from the supernatant by decantation.

For the reaction 1,4-butanediol may be used instead of 1,6-hexanediol, but less of the small particles are yielded.

4. Synthesis of $Y_3Al_5O_{12}$:Nd Nanoparticles (Invisible, Infrared Luminescence):

In an autoclave glass vessel 4.26 g (20.8 mmol) of aluminium isopropoxide, 4.15 g (11.875 mmol) of yttrium acetate.4 $H_2O$, and 215 mg (0.625 mol) of neodymium(III) acetate.1.5 $H_2O$ are mixed with 100 ml of 1,6-hexanediol. The glass vessel is placed in an autoclave and loosely capped with a glass cap. To allow heat transfer to the vessel, the space between the inner wall of the autoclave and the glass vessel is filled with 50 ml of 1,6-hexanediol. Subsequently, the autoclave is closed, carefully evacuated twice and filled each time with nitrogen or argon (or another inert gas). Finally the autoclave is heated to 573 K and kept at this temperature for 4 hours. The autoclave is left to cool down. After the pressure is back to normal, the autoclave is opened. The content of the glass vessel is dissolved in 100–250 ml of isopropanol. The precipitate is collected by centrifugation and washed several times in isopropanol. Subsequently, it is washed with distilled water until peptization starts (=small particles of the precipitate dissolve again). The colloidal solution is centrifuged at 12,000×g for 60 min and the precipitate of the $Y_3Al_5O_{12}$:Nd nanoparticles is separated from the supernatant by decantation.

For the reaction 1,4-butanediol may be used instead of 1,6-hexanediol, but less of the small particles are yielded.

5. Synthesis of $Y_3Al_5O_{12}$:Ce Nanoparticles (Green Luminescence):

In an autoclave glass vessel 4.26 g (20.8 mmol) of aluminium isopropoxide, 4.15 g (11.875 mmol) of yttrium acetate.4 $H_2O$, and 215 mg (0.625 mmol) of cerium(III) acetate.1.5 $H_2O$ are mixed with 100 ml of 1,6-hexanediol. The glass vessel is placed in an autoclave and loosely capped with a glass cap. To allow heat transfer to the vessel, the space between the inner wall of the autoclave and the glass vessel is filled with 50 ml of 1,6-hexanediol. Subsequently, the autoclave is closed, carefully evacuated twice and filled each time with nitrogen or argon (or another inert gas). Finally the autoclave is heated to 573 K and kept at this temperature for 4 hours. The autoclave is left to cool down. After the pressure is back to normal, the autoclave is opened. The content of the glass vessel is dissolved in 100–250 ml of isopropanol. The precipitate is collected by centrifugation and washed several times in isopropanol. Subsequently, it is washed with distilled water until peptization starts (=small particles of the precipitate dissolve again). The colloidal solution is centrifuged at 12,000×g for 60 min and the precipitate of the $Y_3Al_5O_{12}$:Ce nanoparticles is separated from the supernatant by decantation.

Properties of the substance: yellow, not colourless, can also be excited by violet light.

For the reaction 1,4-butanediol may be used instead of 1,6-hexanediol, but less of the small particles are yielded.

6. Synthesis of $Gd_3Ga_5O_{12}$:Tb Nanoparticles:

3.78 g (10.4 mmol) of $Ga(NO_3)_3$.6 $H_2O$, 2.68 g (5.9375 mmol) of $Gd(NO_3)_3$.6 $H_2O$, and 142 mg (0.3125 mmol) of $Tb(NO_3)_3$.6 $H_2O$ are stirred in 20 ml of water until they are dissolved. This solution is poured at one go into a solution consisting of 10 ml of ammonia water (25%) and 40 ml of water (not in reverse order!). The pH value should be over 10, otherwise concentrated ammonia needs to be added. After having collected the precipitate by centrifugation, the supernatant is decanted. The precipitate is washed 5 times in 50–100 ml of water and then resuspended and washed 5 times in 50–100 ml of methanol, followed by centrifugation and decantation. After decantation, the still methanol-moist precipitate is put into a reflux apparatus together with 100 ml of melted 1,6-hexanediol. The apparatus is heated to 373 K under vacuum until methanol and water are completely removed from the reaction mixture by distillation. The apparatus is gassed with an inert gas (e.g. nitrogen or argon) and the mixture is refluxed under a stream of inert gas for 16 hours. The reaction solution is left to cool and then poured into a glass vessel for the autoclave. The glass vessel is placed in an autoclave and loosely capped with a glass cap. To allow heat transfer to the vessel, the space between the inner wall of the autoclave and the glass vessel is filled with 50 ml of 1,6-hexanediol. Subsequently, the autoclave is closed, carefully evacuated twice and filled each time with nitrogen or argon (or another inert gas). Finally the autoclave is heated to 573 K and kept at this temperature for 4 hours. The autoclave is left to cool down. Then the content of the glass vessel is dissolved in 100–250 ml of isopropanol. The precipitate is collected by centrifugation and washed several times in isopropanol. Subsequently, it is washed with distilled water until peptization starts (=small particles of the precipitate dissolve again). The colloidal solution is centrifuged at 12,000×g for 60 min and the precipitate of the $Gd_3Ga_5O_{12}$:Tb nanoparticles is separated from the supernatant by decantation. For the reaction 1,4- butanediol may be used instead of 1,6-hexanediol, but less of the small particles are yielded.

7. Synthesis of $Y_3Al_5O_{12}$:Nd Nanoparticles:

3.90 g (10.4 mmol) of $Al(NO_3)_3.9\ H_2O$, 2.27 g (5.9375 mmol) of $Y(NO_3)_3.6\ H_2O$, and 136 mg (0.3125 mmol) of $Nd(NO_3)_3.6\ H_2O$ are stirred in 20 ml of water until they are dissolved. This solution is poured at one go into a solution consisting of 10 ml of ammonia water (25%) and 40 ml of water (not in reverse order!). The pH value should be over 10, otherwise concentrated ammonia needs to be added. After having collected the precipitate by centrifugation, the supernatant is decanted. The precipitate is washed 5 times in 50–100 ml of water and then resuspended and washed 5 times in 50–100 ml of methanol, followed by centrifugation and decantation. After decantation, the still methanol-moist precipitate is put into a reflux apparatus together with 100 ml of melted 1,6-hexanediol. The apparatus is heated to 373 K under vacuum until methanol and water are completely removed from the reaction mixture by distillation. The apparatus is gassed with an inert gas (e.g. nitrogen or argon) and the mixture is refluxed under a stream of inert gas for 16 hours. The reaction solution is left to cool and then poured into a glass vessel for the autoclave. The glass vessel is placed in an autoclave and loosely capped with a glass cap. To allow heat transfer to the vessel, the space between the inner wall of the autoclave and the glass vessel is filled with 50 ml of 1,6-hexanediol. Subsequently, the autoclave is closed, carefully evacuated twice and filled each time with nitrogen or argon (or another inert gas). Finally the autoclave is heated to 573 K and kept at this temperature for 4 hours. The autoclave is left to cool down. Then the content of the glass vessel is dissolved in 100–250 ml of isopropanol. The precipitate is collected by centrifugation and washed several times in isopropanol. Subsequently, it is washed with distilled water until peptization starts (=small particles of the precipitate dissolve again). The colloidal solution is centrifuged at 12,000×g for 60 min and the precipitate of the $Y_3Al_5O_{12}$:Nd nanoparticles is separated from the supernatant by decantation. For the reaction 1,4-butanediol may be used instead of 1,6-hexanediol, but less of the small particles are yielded.

8. Synthesis of $Y_3Al_5O_{12}$:Ce Nanoparticles:

3.90 g (10.4 mmol) of $Al(NO_3)_3.9\ H_2O$, 2.27 g (5.9375 mmol) of $Y(NO_3)_3.6\ H_2O$, and 136 mg (0.3125 mmol) of $Ce(NO_3)_3.6\ H_2O$ are stirred in 20 ml of water until they are dissolved. This solution is poured at one go into a solution consisting of 10 ml of ammonia water (25%) and 40 ml of water (not in reverse order!). The pH value should be over 10, otherwise concentrated ammonia needs to be added. After having collected the precipitate by centrifugation, the supernatant is decanted. The precipitate is washed 5 times in 50–100 ml of water and then resuspended and washed 5 times in 50–100 ml of methanol, followed by centrifugation and decantation. After decantation, the still methanol-moist precipitate is put into a reflux apparatus together with 100 ml of melted 1,6-hexanediol. The apparatus is heated to 373 K under vacuum until methanol and water are completely removed from the reaction mixture by distillation. The apparatus is gassed with an inert gas (e.g. nitrogen or argon) and the mixture is refluxed under a stream of inert gas for 16 hours. The reaction solution is left to cool and then poured into a glass vessel for the autoclave. The glass vessel is placed in an autoclave and loosely capped with a glass cap. To allow heat transfer to the vessel, the space between the inner wall of the autoclave and the glass vessel is filled with 50 ml of 1,6-hexanediol. Subsequently, the autoclave is closed, carefully evacuated twice and filled each time with nitrogen or argon (or another inert gas). Finally the autoclave is heated to 573 K and kept at this temperature for 4 hours. The autoclave is left to cool down. Then the content of the glass vessel is dissolved in 100–250 ml of isopropanol. The precipitate is collected by centrifugation and washed several times in isopropanol. Subsequently, it is washed with distilled water until peptization starts (=small particles of the precipitate dissolve again). The colloidal solution is centrifuged at 12,000×g for 60 min and the precipitate of the $Y_3Al_5O_{12}$:Ce nanoparticles is separated from the supernatant by decantation. For the reaction 1,4-butanediol may be used instead of 1,6-hexanediol, but less of the small particles are yielded.

9. Synthesis of $Y_3Al_5O_{12}$:Eu Nanoparticles:

3.90 g (10.4 mmol) of $Al(NO_3)_3.9\ H_2O$, 2.27 g (5.9375 mmol) of $Y(NO_3)_3.6\ H_2O$, and 139 mg (0.3125 mmol) of $Eu(NO_3)_3.6\ H_2O$ are stirred in 20 ml of water until they are dissolved. This solution is poured at one go into a solution consisting of 10 ml of ammonia water (25%) and 40 ml of water (not in reverse order!). The pH value should be over 10, otherwise concentrated ammonia needs to be added. After having collected the precipitate by centrifugation, the supernatant is decanted. The precipitate is washed 5 times in 50–100 ml of water and then resuspended and washed 5 times in 50–100 ml of methanol, followed by centrifugation and decantation. After decantation, the still methanol-moist precipitate is put into a reflux apparatus together with 100 ml of melted 1,6-hexanediol. The apparatus is heated to 373 K under vacuum until methanol and water are completely removed from the reaction mixture by distillation. The apparatus is gassed with an inert gas (e.g. nitrogen or argon) and the mixture is refluxed under a stream of inert gas for 16 hours. The reaction solution is left to cool and then poured into a glass vessel for the autoclave. The glass vessel is placed in an autoclave and loosely capped with a glass cap. To allow heat transfer to the vessel, the space between the inner wall of the autoclave and the glass vessel is filled with 50 ml of 1,6-hexanediol. Subsequently, the autoclave is closed, carefully evacuated twice and filled each time with nitrogen or argon (or another inert gas). Finally the autoclave is heated to 573 K and kept at this temperature for 4 hours. The autoclave is left to cool down. Then the content of the glass vessel is dissolved in 100–250 ml of isopropanol. The precipitate is collected by centrifugation and washed several times in isopropanol. Subsequently, it is washed with distilled water until peptization starts (=small particles of the precipitate dissolve again). The colloidal solution is centrifuged at 12,000×g for 60 min and the precipitate of the $Y_3Al_5O_{12}$:Eu nanoparticles is separated from the supernatant by decantation. For the reaction 1,4-butanediol may be used instead of 1,6-hexanediol, but less of the small particles are yielded.

10. Luminescent and Doped Zinc Silicate:

Preparation of Manganese-doped $Zn_2SiO_4$ (3-at %):

In a PE vessel with cap 2.885 g (9.7 mmol) of $Zn(NO_3)_2.6\ H_2O$ and 8 g of NaOH pellets are placed, 80 ml of water is added, and the mixture is stirred overnight in the closed vessel. In a second PE vessel 8 g of NaOH pellets are dissolved in 80 ml of water. 1.042 g (5 mmol) of $Si(OC_2H_5)_4$ (tetraethoxysilane) or 0.761 g (5 mmol) of $Si(OCH_3)_4$ (tetramethoxysilane) are added, and the reaction mixture is stirred in the closed vessel overnight. 48 mg (0.3 mol) of $KMnO_4$ are dissolved in a small amount of water. All three solutions are placed in an autoclave which is filled to 190 ml. The autoclave is closed and gassed with forming gas ($H_2$/$N_2$=10/90 or 5/95) for 30 min. The reaction mixtures are heated to 273 K and stirred (600 rpm) overnight. The precipitate obtained is collected by centrifugation, washed with distilled water until peptization starts (=small particles of the precipitate dissolve again). The colloidal solution is centrifuged at 12,000×g for 60 min and the precipitate of the nanoparticles is separated from the supernatant by decantation.

11. Luminescent and Doped Barium Silicate:
Preparation of Lead-doped BaSiO$_3$ (2-at %):

1.042 g (5 mmol) of Si(OC$_2$H$_5$)$_4$ are placed in a 100 ml PE bottle. In a beaker 65 mg (0.16 mmol) of Pb(ClO$_4$)$_2$.3 H$_2$O are dissolved in a few drops of water and 30 ml of a 0.1 M Ba(OH)$_2$ solution are added. The clear solution is poured to the tetraethoxysilane. The beaker is rinsed with another 50 ml of the 0.1 M Ba(OH)$_2$ solution which are also poured into the PE bottle. The solution is stirred for 60 min in the well-closed PE bottle. Subsequently, the suspension is poured into a Teflon autoclave vessel, stirred and heated overnight in the autoclave at a temperature of 543 K. The precipitate obtained is collected by centrifugation and washed twice with water. Then it is washed with distilled water until peptization starts (=small particles of the precipitate dissolve again). The colloidal solution is centrifuged at 12,000×g for 60 min and the precipitate of the nanoparticles is separated from the supernatant by decantation.

12. Luminescent and Doped Calcium Silicate:
Preparation of Lead-doped CaSiO$_3$ (2-at %):

In a 100 ml conical flask 40 ml of ethanol are added to 1.042 g (5 mmol) of Si(OC$_2$H$_5$)$_4$, and the mixture is stirred. The pH value of 50 ml of water is adjusted to 4.5 with HNO$_3$ which is then added to the stirred solution. The conical flask is closed and stirred overnight. If the solution remained clear, 40 ml of water are put into a 250 ml round-bottom flask which is tilted to its position on a rotary evaporator. The position of the meniscus is marked on the glass wall of the flask using a water-proof pen. Then the water is poured out and the solution of the conical flask is poured into the round-bottom flask. To remove the alcohol, the solution is evaporated with a rotary evaporator (bath temperature 313 K) until about 40 ml (marked line) are left. 1.157 g (4.9 mmol) of Ca(NO$_3$)$_2$.4 H$_2$O and 33 mg (0.1 mol) of Pb(NO$_3$)$_2$ are dissolved in 30 ml of water. The pH values of this solution and of the silicate solution are carefully adjusted to 6.0 with diluted KOH. Then, the Ca/Pb solution is poured into the silicate solution and the mixture is poured into a glass autoclave vessel. The vessel is closed and heated overnight in an autoclave at a temperature of 543 K with stirring. The precipitate obtained is collected by centrifugation and washed twice with water. Then it is washed with distilled water until peptization starts (=small particles of the precipitate dissolve again). The colloidal solution is centrifuged at 12,000×g for 60 min and the precipitate of the nanoparticles is separated from the supernatant by decantation.

13. GdVO$_4$:Eu Colloids:
Preparation of Gd$_{0.95}$Eu$_{0.05}$VO$_4$ 4.117 g (9.5 mol) of Gd(NO$_3$)$_3$.5 H$_2$O and 223 mg (0.5 mmol) of Eu(NO$_3$)$_3$.6 H$_2$O are dissolved in 20 ml of water. The solution is added to 15 ml of a 1 M NaOH solution in a Teflon autoclave vessel. 1.820 g (5 mmol) of Na$_3$VO$_4$.10 H$_2$O are dissolved in 35 ml of water and added to the lanthanide solution. The solution (Teflon vessel) is heated in an autoclave to 543 K for 1 hour with stirring. The precipitate is collected by filtration and is stirred for 60 min in 100 ml of a 0.5 M HNO$_3$ solution to which 6.87 g of a 60% Dequest 2010 solution (Monsanto) (20 mmol) have been added. The pH of the mixture is then adjusted to 5 with a 1 M NaOH solution (approx. 40–100 ml!), and the precipitate is collected by centrifugation at 4500 rpm for 15 min. The precipitate is washed with distilled water until peptization starts (=small particles of the precipitate dissolve again). The colloidal solution is centrifuged at 12,000×g for 60 min and the precipitate of the nanoparticles is separated from the supernatant by decantation.

14. Luminescent Calcium Tungstate:
Preparation:

779 mg (3.3 mmol) of Ca(NO$_3$)$_2$.4 H$_2$O are dissolved in 150 ml of water, the solution is split into three portions and the pH value is adjusted to 12 with NaOH. 990 mg (3 mmol) of Na$_2$WO$_4$.2 H$_2$O are dissolved in 150 ml of water and this solution is also brought to pH 12. The solutions are mixed in autoclave vessels, if necessary, the pH values are adjusted to the previous values, and the vessels are heated overnight in an autoclave to 543 K with stirring. The precipitates obtained are collected by centrifugation and washed with water. Subsequently, they are washed with distilled water until peptization starts (=small particles of the precipitate dissolve again). The colloidal solution is centrifuged at 12,000×g for 60 min and the precipitate is separated from the supernatant by decantation.

15. Y$_2$(WO$_4$)$_3$:Eu Colloids:
Preparation of Y$_{0.9}$Eu$_{0.1}$)$_2$ (WO$_4$)$_3$:

4.948 g (15 mmol) of Na$_2$WO$_4$.2 H$_2$O are dissolved in 35 ml of water, and 5 ml of a 1 M NaOH solution are added to bring the solution to approx. pH 13. 3.447 g (9 mmol) of Y(NO$_3$)$_3$.6 H$_2$O and 446 mg (0.1 mmol) Of Eu(NO$_3$)$_3$. 6 H$_2$O are dissolved in 30 ml of water and are added to the tungstate solution with stirring. The pH value is adjusted to ≧10. The solution is heated overnight in an autoclave at a filling degree of 70% to 533 K with stirring. Subsequently, the precipitate is washed with distilled water until peptization starts (small particles of the precipitate dissolve again). The colloidal solution is centrifuged at 12,000×g for 60 min and the precipitate of the nanoparticles is separated from the supernatant by decantation.

16. Luminescent and Doped Calcium Molybdate:
Preparation of Europium-doped CaMoO$_4$ (5-at %):

708 mg (3.0 mmol) of Ca(NO$_3$)$_2$.4 H$_2$O and 74 mg (0.167 mmol) of Eu(NO$_3$)$_3$.6 H$_2$O are dissolved in 30 ml of water. 618 mg (3.5 mmol of Mo) of (NH$_4$)$_6$Mo$_7$O$_{24}$.4 H$_2$O are dissolved in 30 ml of water and the solution is brought to pH 8 with a 1 M NaOH solution. The Ca/Eu solution is added to the molybdate solution in a Teflon autoclave vessel, the pH value, if necessary, is adjusted to the previous pH value of the molybdate solution, and the mixture is heated overnight in an autoclave at 543 K with stirring. The precipitates obtained are collected by centrifugation and washed with water. Subsequently, it is washed with distilled water until peptization starts (=small particles of the precipitate dissolve again). The colloidal solution is centrifuged at 12,000×g for 60 min and the precipitate of the nanoparticles is separated from the supernatant by decantation.

17. GdTaO$_4$:Tb Colloids:
Preparation of K$_8$Ta$_6$O$_{19}$.16 H$_2$O (MW=1990.07 g/mol):

An oven is preheated to 773 K. 25 g of KOH and 5 g of Ta$_2$O$_5$ are filled into a silver crucible which is covered with an Ag-metal sheet and heated for 30 min in the oven until a clear melt flux is achieved. In the meantime 500 ml of distilled water are heated to boiling point. The crucible is taken from the oven, left to cool and the melt is leached several times using small amounts of hot water (around 50–100 ml altogether, if sufficient). The resulting solution is filled into a PE bottle (don't use glass). The solution is filtrated using a fluted filter and a plastic funnel into a PE bottle. To precipitate the product, an equal to 4-fold volume of ethanol (technical quality is sufficient) is added to the solution. The supernatant is decanted, if necessary after centrifugation. The precipitate is dissolved another two times in a KOH solution (approx. 0.1 M) followed by precipitation with ethanol. It is then dried onto filter paper in a desiccator (silica gel) and filled into a bottle. (A yield of 100%=7.5 g cannot be achieved due to the formation of $KTaO_3$.)

1. Preparation of $Gd_{0.95}Tb_{0.05}TaO_4$:

2.058 g (4.75 mmol) of $Gd(NO_3)_3.5\,H_2O$ and 109 mg (0.25 mmol) $Tb(NO_3)_3.5\,H_2O$ are dissolved in 20 ml of water and are added to 14 ml of a 1 M KOH solution in a Teflon autoclave vessel. 1.66 g of $K_8Ta_6O_{19}.16\,H_2O$ (5 mmol of Ta) and 1 ml of a 1 M KOH solution are dissolved in 35 ml of water and are added to the lanthanide solution. The solution is heated in an autoclave (Teflon vessel) to 543 K for one hour with stirring. The precipitate is collected by filtration and is stirred for 60 min in 200 ml of a 0.5 $HNO_3$ solution (pH 0.3) to which 6.87 g of a 60% Dequest 2010 solution (20 mmol) have been added. Then the pH value is adjusted to 12.5 with a KOH solution that has a higher molarity than 1 M (approx. 80–200 ml are needed using a 1 M solution!). The mixture is stirred overnight and then centrifuged for 10 min at 4500 rpm. The supernatant is completely decanted and discarded.

The precipitate is suspended in 40 ml of water and dispersed for 2 min in an ultrasound bath. Subsequently, the suspension is centrifuged for 15 min at 4500 rpm. The supernatant is decanted (peptization?) and stored. The resuspending of the precipitate followed by centrifugation is repeated for another three times. Subsequently, the precipitate is washed with water until peptization starts (=small particles of the precipitate dissolve again). The colloidal solution is centrifuged at 12,000×g for 60 min and the precipitate is separated from the supernatant by decantation.

18. Preparation of $Ca_3(PO_4)_2:Eu^{2+}$ Nanoparticles:

300 ml of tris(ethylhexyl) phosphate is purged by nitrogen to displace all oxygen. Then a solution consisting of 10.48 g (71.25 mmol) of $CaCl_2.2\,H_2O$ and 836 mg (3.75 mmol) of $EuCl_2$ in 100 ml of dry methanol is added. The reaction mixture is distilled at a temperature of 303 to 313 K under vacuum until the methanol and the water of crystallization are removed. Subsequently, 4.90 g (50 mmol) of crystalline phosphoric acid are dissolved in a mixture consisting of 65.5 ml (150 mmol) of trioctylamine and 150 ml of tris(ethylhexyl) phosphate which is then added to the reaction mixture. The solution is evacuated several times and gassed with nitrogen to minimize oxidation to $Eu^{3+}$. Subsequently, the reaction mixture is heated to 472 K. During the heating, some of the solvent is degraded and as a consequence the boiling point of the mixture decreases. As soon as the reaction mixture boils at a temperature of 443 to 448 K, it is left to cool and a 4-fold amount of methanol is added. The resulting precipitate is collected by centrifugation, washed several times with methanol and dried.

19. Preparation of $Ca_3(PO_4)_2:Eu^{2+}, Mn^{2+}$ Nanoparticles:

300 ml of tris(ethylhexyl) phosphate is purged by nitrogen to displace all oxygen. Then a solution consisting of 9.78 g (70 mmol) of $CaCl_2.2\,H_2O$, 223 mg (1 mmol) of $EuCl_2$, and 503 mg (4 mmol) of $MnCl_2$ in 100 ml of dry methanol is added. The reaction mixture is distilled at a temperature of 303 to 313 K under vacuum until the methanol and the water of crystallization are completely removed. Subsequently, 4.90 g (50 mmol) of crystalline phosphoric acid are dissolved in a mixture consisting of 65.5 ml (150 mmol) of trioctylamine and 150 ml of tris(ethylhexyl) phosphate which is then added to the reaction mixture. The solution is evacuated several times and gassed with nitrogen to minimize oxidation to $Eu^{3+}$. Subsequently, the reaction mixture is heated to 472 K. During the heating, some of the solvent is degraded and as a consequence the boiling point of the mixture decreases. As soon as the reaction mixture boils at a temperature of 443 to 448 K, it is left to cool and a 4-fold amount of methanol is added. The resulting precipitate is collected by centrifugation, washed several times with methanol and dried.

20. Preparation of $BaAl_2O_4:Eu^{2+}$ nanoparticles:

4.09 g (20 mmol) of aluminium isopropoxide, 2.43 g (9.5 mmol) of barium di-isopropylate, and 111 mg (0.5 mmol) of $EuCl_2$ are poured with 100 ml of 1,6-hexanediol into an autoclave glass vessel. The glass vessel is placed in an autoclave and loosely capped with a glass cap. To allow heat transfer to the vessel, the space between the inner wall of the autoclave and the glass vessel is filled with 50 ml of 1,6-hexanediol. Subsequently, the autoclave is closed, carefully evacuated twice and filled each time with nitrogen or argon (or another inert gas). Finally the autoclave is heated to 573 K and kept at this temperature for 4 hours. The autoclave is left to cool down. After the pressure is back to normal, the autoclave is opened. The content of the glass vessel is dissolved in 100–250 ml of isopropanol. The precipitate is collected by centrifugation and washed several times in isopropanol. Subsequently, it is washed with distilled water until peptization starts (=small particles of the precipitate dissolve again). The colloidal solution is centrifuged at 12,000×g for 60 min and the precipitate of the $BaAl_2O_4:Eu$ nanoparticles is separated from the supernatant by decantation.

For the reaction 1,4-butanediol may be used instead of 1,6-hexanediol, but less of the small particles are yielded.

Further synthesis embodiments of the invention are exemplarily given in the following paragraph:

21. Manganese-doped Zinc Silicate Nanoparticles:

2.5 of tetraethyl orthosilicate are mixed with 40 ml of ethanol. 7.5 ml of a 0.8 M solution of tetrabutylammonium hydroxide in methanol are added. 0.9 ml of water is added under stirring, and the reaction mixture is stirred overnight in a closed vessel. Subsequently, approx. 20 ml of dihexyl ether are poured to the solution, and the alcohols are removed with a rotary evaporator (bath temperature around 30° C.).

1.3 g (9.5 mmol) of $ZnCl_2$ and 99 mg (0.5 mmol) of $MnCl_2.4\,H_2O$ are dissolved in a small amount of methanol. 3.3 ml (12 mmol) of tributyl phosphate and 40 ml of dihexyl ether are added. The methanol is removed by distillation under vacuum. While the solution is stirred, 16.6 ml (38 mmol) of trioctylamine and the above-scribed solution of tetrabutylammonium silicate solution in dihexyl ether are added. Subsequently, the mixture is heated to approx. 200° C. under nitrogen and stirred overnight at this temperature.

The solvent (particularly the dihexyl ether) is removed from the solution by distillation under vacuum.

If desired, any by-products can be removed from the remaining raw product by washing with small amounts of ethanol as described above, by diafiltration or by other standard purification procedures.

22. Manganese-doped Zinc Silicate Nanoparticles:

2.5 of tetraethyl orthosilicate are mixed with 40 ml of ethanol. 7.5 ml of a 0.8 M solution of tetrabutylammonium hydroxide in methanol are added. 0.9 ml of water is added under stirring, and the reaction mixture is stirred overnight in a closed vessel. Subsequently, approx. 20 ml of dihexyl ether are poured to the solution, and the alcohols are removed with a rotary evaporator (bath temperature around 30° C. ).

1.3 g (9.5 mmol) of $ZnCl_2$ and 99 mg (0.5 mmol) of $MnCl_2.4\ H_2O$ are dissolved in a small amount of methanol, and 50 ml of bis(2-ethylhexyl)amine are added. The methanol is removed by distillation under vacuum. While the solution is stirred, the above-described solution of tetrabutylammonium silicate solution in dihexyl ether is added. Subsequently, the mixture is heated to approx. 200° C. under nitrogen and stirred overnight at this temperature.

The solvent (particularly the dihexyl ether) is removed from the solution by distillation under vacuum.

The remaining raw product can be purified in a stirring cell by diafiltration (pore size of the filter: 5,000–10,000 Dalton) against toluene and can be isolated by subsequent concentration of the diafiltrated solution with a rotary evaporator.

23. Lead-doped Calcium Silicate Nanoparticles:

2.5 of tetraethyl orthosilicate are mixed with 40 ml of ethanol. 7.5 ml of a 0.8 M solution of tetrabutylammonium hydroxide in methanol are added. 0.9 ml of water is added under stirring, and the reaction mixture is stirred overnight in a closed vessel. Subsequently, approx. 20 ml of dibenzyl ether are poured to the solution, and the alcohols are removed with a rotary evaporator (bath temperature around 30° C.).

1.67 g (9.5 mmol) of $Ca(CH_3COO)_2.H_2O$ and 222 mg (0.5 mmol) of $Pb(CH_3COO)_2.3\ H_2O$ are dissolved in a small amount of methanol. 3.3 ml (12 mmol) of tributyl phosphate and 40 ml of dibenzyl ether are added. The methanol is removed by distillation under vacuum. While the solution is stirred, 16.6 ml (38 mmol) of trioctylamine and the above-described solution of tetrabutylammonium silicate solution in dibenzyl ether are added. Subsequently, the mixture is heated to approx. 250° C. under nitrogen and stirred overnight at this temperature.

Subsequently, the solution is purified in a stirring cell by diafiltration (pore size of the filter: 5000–10,000 Dalton) against toluene, and the nanoparticles are isolated by subsequent concentration of the diafiltrated solution with a rotary evaporator.

24. Cerium-doped Yttrium Silicate Nanoparticles:

2.5 of tetraethyl orthosilicate are mixed with 40 ml of ethanol. 7.5 ml of a 0.8 M solution of tetrabutylammonium hydroxide in methanol are added. 0.9 ml of water is added under stirring, and the reaction mixture is stirred overnight in a closed vessel. Subsequently, approx. 20 ml of dibenzyl ether are poured to the solution, and the alcohols are removed with a rotary evaporator (bath temperature around 30° C.).

2.88 g (9.5 mmol) of $YCl_3.6\ H_2O$ and 177 mg (0.5 mmol) of $CeCl_3.6\ H_2O$ are dissolved in a small amount of methanol. 3.3 ml (12 mmol) of triisobutyl phosphate and 40 ml of dibenzyl ether are added. The methanol is removed by distillation under vacuum. While the solution is stirred, 16.6 ml (38 mmol) of trioctylamine and the above-described solution of tetrabutylammonium silicate solution in dibenzyl ether are added. Subsequently, the mixture is heated to approx. 250° C. under nitrogen and stirred overnight at this temperature.

Subsequently, the solution is purified in a stirring cell by diafiltration (pore size of the filter: 5000–10,000 Dalton) against toluene, and the nanoparticles are isolated by subsequent concentration of the diafiltrated solution with a rotary evaporator.

25. Terbium-doped Yttrium Silicate Nanoparticles:

2.5 of tetraethyl orthosilicate are mixed with 40 ml of ethanol. 7.5 ml of a 0.8 M solution of tetrabutylammonium hydroxide in methanol are added. 0.9 ml of water is added under stirring, and the reaction mixture is stirred overnight in a closed vessel. Subsequently, approx. 20 ml of dioctyl ether are poured to the solution, and the alcohols are removed with a rotary evaporator (bath temperature around 30° C.).

2.88 g (9.5 mmol) of $YCl_3.6\ H_2O$ and 187 mg (0.5 mmol) of $TbCl_3.6\ H_2O$ are dissolved in a small amount of methanol. 3.3 ml (12 mmol) of tributyl phosphate and 40 ml of dibenzyl ether are added. The methanol is removed by distillation under vacuum. While the solution is stirred, 16.6 ml (38 mmol) of tris(2-ethylhexyl)amine and the above-described solution of tetrabutylammonium silicate solution in dioctyl ether are added. Subsequently, the mixture is heated to approx. 250° C. under nitrogen and stirred overnight at this temperature.

Subsequently, the solution is purified in a stirring cell by diafiltration (pore size of the filter: 5000–10,000 Dalton) against toluene, and the nanoparticles are isolated by subsequent concentration of the diafiltrated solution with a rotary evaporator.

26. $LaBO_3$:Eu Nanoparticles:

3.528 g (9.5 mmol) of $LaCl_3.7\ H_2O$ and 183 mg (0.5 mmol) of $EuCl_3.6\ H_2O$ are dissolved in a small amount of methanol. 3.3 ml (12 mmol) of tributyl phosphate and 40 ml of dihexyl ether are added. The methanol and the released water of crystallisation are removed by distillation under vacuum. While the solution is stirred, 16.6 ml (38 mmol) of trioctylamine and 14.0 ml of a 1 M solution of boric acid ($H_3BO_3$) in dihexyl ether (14 mmol) are added. Subsequently, the mixture is heated to approx. 200° C. under nitrogen and stirred overnight at this temperature. The solvent (particularly the dihexyl ether) is removed from the solution by distillation under vacuum.

If desired, any by-products can be removed from the remaining raw product by washing with small amounts of ethanol as described above, by diafiltration or by other standard purification procedures.

27. $InBO_3$:Tb Nanoparticles:

2.78 g (9.5 mmol) of $InCl_3.4\ H_2O$ and 187 mg (0.5 mmol) of $TbCl_3.6\ H_2O$ are dissolved in a small amount of ethanol. 4.6 g (12 mmol) of trioctylphosphine oxide (TOPO) dissolved in 40 ml of dioctyl ether are added. The methanol and the released water of crystallisation are removed by distillation under vacuum.

To the cloudy solution, 16.6 ml of tris(2-ethylhexyl)amine and 14.0 ml of a 1 M solution of boric acid ($H_3BO_3$) in dioctyl ether (14 mmol) are added. Subsequently, the mixture is heated to approx. 280° C. under nitrogen and stirred overnight at this temperature.

Subsequently, the solution is purified in a stirring cell by diafiltration pore size of the filter: 5000–10,000 Dalton) against toluene, and the nanoparticles are isolated by subsequent concentration of the diafiltrated solution with a rotary evaporator.

28. $YBO_3$:Eu Nanoparticles:

2.88 g (9.5 mmol) of $YCl_3.6\ H_2O$ and 183 mg (0.5 mmol) of $EuCl_3.6\ H_2O$ are dissolved in a small amount of ethanol. 3.3 ml (12 mmol) of tributyl phosphate and 40 ml of dihexyl ether are added. The ethanol and the released water of crystallisation are removed by distillation under vacuum.

While the solution is stirred, 12.9 ml (38 mmol) of trihexylamine and 14.0 ml of a 1 M solution of boric acid ($H_3BO_3$) in dihexyl ether (14 mmol) are added. Subsequently, the mixture is heated to approx. 200° C. under nitrogen and stirred overnight at this temperature.

The dihexyl ether is removed from the solution by distillation under vacuum.

If desired, any by-products can be removed from the remaining raw product by washing with small amounts of ethanol as described above, by diafiltration or by other standard purification procedures.

29. $LaAsO_4$:Eu Nanoparticles:

1.38 g of $As_2O_5$ are suspended in approx. 40 ml of methanol. 1.0 ml of water and 3.8 ml of a 0.8 M solution of tetrabutylammonium hydroxide in methanol are added and the mixture is stirred in a closed vessel overnight. Subsequently, 20 ml of dihexyl ether are poured to the solution, and the alcohols are removed with a rotary evaporator (bath temperature around 30° C.).

3.528 g (9.5 mmol) of $LaCl_3.7$ $H_2O$ and 183 mg (0.5 mmol) of $EuCl_3.6$ $H_2O$ are dissolved in a small amount of methanol. 3.3 ml (12 mmol) of tributyl phosphate and 40 ml of dihexyl ether are added. The methanol and the released water of crystallisation are removed by distillation under vacuum.

While the solution is stirred, 16.6 ml (38 mmol) of trioctylamine and the above-described arsenate solution are added. Subsequently, the mixture is heated to approx. 200° C. under nitrogen and stirred overnight at this temperature.

The solvent (particularly the dihexyl ether) is red from the solution by distillation under vacuum. If desired, any by-products can be removed from the raw product by washing with small amounts of ethanol, by diafiltration or by other standard purification procedures.

30. $LaAsO_4$:Eu Nanoparticles:

3.528 g (9.5 mmol) of $LaCl_3.7H_2O$ and 183 mg (0.5 mmol) of $EuCl_3.6$ $H_2O$ are dissolved in a small amount of methanol. 3.3 ml (12 mmol) of tributyl phosphate and 40 ml of dihexyl ether are added. The methanol and the released water of crystallisation are removed by distillation under vacuum.

While the mixture is stirred, a solution consisting of 3.77 g (12 mmol) of $Na_2HAsO_4.7$ $H_2O$ in 40 ml of tris[2-(2-methoxyethoxy)ethyl]amine (a complexing agent for sodium ions) is added. The mixture is then heated to approx. 200° C. under nitrogen and stirred overnight at this temperature.

Subsequently, the solution is purified in a stirring cell by diafiltration (pore size of the filter: 5000–10,000 Dalton) against ethanol, and the nanoparticles are isolated by subsequent concentration of the diafiltrated solution with a rotary evaporator.

31. $YPO_4$:Ce Nanoparticles:

2.88 g (95 mmol) of $YCl_3.6$ $H_2O$ and 177 mg (0.5 mmol) of $CeCl_3.6$ $H_2O$ are dissolved in a small amount of methanol. 3.3 ml (12 mmol) of tributyl phosphate and 40 ml of dihexyl ether are added. The methanol and the released water of crystallisation are removed by distillation under vacuum.

While the mixture is stirred, a solution consisting of 2.14 g (12 mmol) of $Na_2HPO_4.2$ $H_2O$ in 40 ml of tris[2-(2-methoxyethoxy)ethyl]amine (a complexing agent for sodium ions) is added. The mixture is then heated to approx. 200° C. under nitrogen and stirred overnight at this temperature.

Subsequently, the solution is purified in a stirring cell by diafiltration (pore size of the filter: 5000–10,000 Dalton) against ethanol, and the nanoparticles are isolated by subsequent concentration of the diafiltrated solution with a rotary evaporator.

32. $YPO_4$:Dy Nanoparticles:

28.8 g (9.5 mmol) of $YCl_3.6$ $H_2O$ and 188 mg (0.5 mmol) of $DyCl_3.6$ $H_2O$ are dissolved in a small amount of methanol. 3.3 ml (12 mmol) of triisobutyl phosphate and 40 ml of dihexyl ether are added. The methanol and the released water of crystallization are removed by distillation under vacuum.

2.14 g (12 mmol) of $Na_2HPO_4.2$ $H_2O$ are dissolved in a mixture consisting of 10 ml of 15-crown-5 crown ether (a complexing agent for sodium ions) and 20 ml of dihexyl ether and are poured to the metal salt solution with stirring. The mixture is then heated to approx. 200° C. under nitrogen and stirred overnight at this temperature.

The solvent (particularly the dihexyl ether) is removed from the solution by distillation under vacuum. Subsequently, the solution is purified in a stirring cell by diafiltration (pore size of the filter: 5000–10,000 Dalton) against ethanol, and the nanoparticles are isolated by subsequent concentration of the diafiltrated solution with a rotary evaporator.

33. $In_2S_3$ Nanoparticles:

2.93 g (10 mmol) of $InCl_3.4$ $H_2O$ are dissolved in a small amount of ethanol. 4.6 g (12 mmol) of trioctylphosphine oxide (TOPO) dissolved in 40 ml of dioctyl ether are added. The methanol and the released water of crystallisation are removed by distillation under vacuum.

667 mg (9 mmol) of $NaHS.H_2O$ are dissolved together with 5 ml of 15-crown-5 crown ether (a complexing agent for sodium ions) in 20 ml of ethylene glycol dibutyl ether and are poured to the metal salt solution with stirring. Subsequently, the mixture is heated to approx. 200° C. under nitrogen and stirred overnight at this temperature.

The solvent is removed from the solution by distillation under vacuum. Subsequently, the solution is purified in a stirring cell by diafiltration (pore size of the filter: 5000–10,000 Dalton) against ethanol, and the nanoparticles are isolated by subsequent concentration of the diafiltrated solution with a rotary evaporator.

34. $BaSO_4$:Ce Nanoparticles:

3.165 g (9.5 mmol) of $BaBr_2.2$ $H_2O$ and 177 mg (0.5 mmol) of $CeCl_3.6$ $H_2O$ are dissolved in a small amount of methanol. 3.3 ml (12 mmol) of tributyl phosphate and 40 ml of dihexyl ether are added. The methanol and the released water of crystallisation are removed by distillation under vacuum.

1.66 g (12 mmol) of $NaHSO_4.H_2O$ are dissolved together with 5 ml of 15-crown-5 crown ether (a complexing agent for sodium ions) in 20 ml of ethylene glycol dibutyl ether and are poured to the metal salt solution with stirring. Subsequently, the mixture is heated to approx. 200° C. under nitrogen and stirred overnight at this temperature.

The solvent is removed from the solution by distillation under vacuum. Subsequently, the solution is purified in a stirring cell by diafiltration (pore size of the filter: 5000–10,000 Dalton) against ethanol, and the nanoparticles are isolated by subsequent concentration of the diafiltrated solution with a rotary evaporator.

35. $BaSO_4$:Eu Nanoparticles:

3.165 g (9.5 mmol) of $BaBr_2.2$ $H_2O$ and 183 mg (0.5 mmol) of $EuCl_3.6$ $H_2O$ are dissolved in a small amount of methanol. 3.3 ml (12 mmol) of tributyl phosphate and 40 ml of dihexyl ether are added. The methanol and the released water of crystallisation are removed by distillation under vacuum.

2.05 g (12 mmol) of tetrabutylammonium hydrogensulphate $(CH_2CH_2CH_2CH_2)_4NHSO_4$ are dissolved in 20 ml of dihexyl ether and added together with 16.6 ml (38 mmol) of trioctylamine to the metal salt solution with stirring. Subsequently, the mixture is heated to approx. 200° C. under nitrogen and stirred overnight at this temperature.

The solvent is removed from the solution by distillation under vacuum. Subsequently, the solution is purified in a stirring cell by diafiltration (pore size of the filter: 5000–10,000 Dalton) against ethanol, and the nanoparticles are isolated by subsequent concentration of the diafiltrated solution with a rotary evaporator.

36. $LaF_3$:Ce, Nd Nanoparticles:

1.485 g (4 mmol) of $LaCl_3.7 H_2O$, 1.676 g (4.5 mmol) of $CeCl_3.7 H_2O$, and 538 mg (1.5 mmol) of $NdCl_3.6 H_2O$ are dissolved in a small amount of methanol. 3.3 ml (12 mmol) of tributyl phosphate and 40 ml of dihexyl ether are added. The methanol and the released water of crystallisation are removed by distillation under vacuum.

645 mg (4 mmol) of triethylamine trishydrofluoride $(CH_2CH_2)_4N.3$ HF are dissolved in 20 ml of dihexyl ether and added together with 16.6 ml (38 mmol) of trioctylamine to the metal salt solution with stirring. Subsequently, the mixture is heated to approx. 200° C. under nitrogen and stirred overnight at this temperature.

The solvent is removed from the solution by distillation under vacuum.

If desired, any by-products can be removed from the remaining raw product by washing with small amounts of ethanol as described above, by diafiltration or by other standard purification procedures.

37. $LaF_3$:Ce, Tb Nanoparticles:

1.96 g (4 mmol) of $La(CH_3COCHCOCH_3)_3.3 H_2O$, 2.21 g (4.5 mmol) of $Ce(CH_3COCHCOCH_3)_3.3 H_2O$, and 765 mg (1.5 mmol) of $Tb(CH_3COCHCOCH_3)_3.3 H_2O$ are dissolved in a small amount of methanol. 3.3 ml (12 mmol) of tributyl phosphate and 40 ml of dihexyl ether are added. The methanol and the released water of crystallisation are removed by distillation under vacuum.

0.5 ml of hydrogen fluoride pyridine complex $(C_5H_5N).x$ HF containing approx. 70% (w/v) HF is dissolved in 20 ml of dihexyl ether and is added to the metal acetyl acetonate solution with stirring. Subsequently, the mixture is heated to approx. 200° C. under nitrogen and stirred overnight at this temperature.

The solvent is removed from the solution by distillation under vacuum.

If desired, any by-products can be removed from the remaining raw product by washing with small amounts of ethanol as described above or by diafiltration.

38. $YF_3$:Yb, Er Nanoparticles:

2.10 g (7.9 mmol) of $Y(CH_3CHOCH_3)_3$, 630 mg (1.8 mmol) of $Yb(CH_3CHOCH_3)_3$, and 103 mg (0.3 mmol) of $Er(CH_3CHOCH_3)_3$ are dissolved in a small amount of methanol. 3.3 ml (12 mmol) of tributyl phosphate and 40 ml of dihexyl ether are added. The methanol and the released water of crystallisation are removed by distillation under vacuum.

1.1 g of hydrogen fluoride 2,4,6-trimethyl pyridine complex (approx. 11–12 mmol HF per gram) are dissolved in 20 ml of dihexyl ether and are added to the metal isopropylate solution with stirring. Subsequently, the mixture is heated to approx. 200° C. under nitrogen and stirred overnight at this temperature.

The solvent is removed from the solution by distillation under vacuum.

If desired, any byproducts can be removed from the remaining raw product by washing with small amounts of ethanol as described above or by diafiltration.

39. $LaF_3$:Yb, Er Nanoparticles:

2.50 g (7.9 mmol) of $La(CH_3CHOCH_3)_3$, 630 mg (1.8 mmol) of $Yb(CH_3CHOCH_3)_3$, and 103 mg (0.3 mmol) of $Er(CH_3CHOCH_3)_3$ are dissolved in a small amount of methanol. 3.3 ml (12 mmol) of tributyl phosphate and 40 ml of dihexyl ether are added. The methanol and the released water of crystallisation are removed by distillation under vacuum.

645 mg (4 mmol) of triethylamine trishydrogen fluoride $(CH_2CH_2)_4N.3$ HF are dissolved in 20 ml of dihexyl ether and are added to the metal isopropylate solution with stirring. Subsequently, the mixture is heated to approx. 200° C. under nitrogen and stirred overnight at this temperature.

The solvent is removed from the solution by distillation under vacuum.

If desired, any by-products can be removed from the remaining raw product by washing with small amounts of ethanol as described above or by diafiltration.

40. $CeF_3$:Nd Nanoparticles:

3.11 g (9.8 mmol) of $Ce(CH_3CHOCH_3)_3$ and 64 mg (0.2 mmol) of $Nd(CH_3CHOCH_3)_3$ are dissolved in a small amount of methanol. 3.3 ml (12 mmol) of tributyl phosphate and 40 ml of diisopentyl ether are added. The methanol and the released water of crystallisation are removed by distillation under vacuum.

0.5 ml of a 48% solution of hydrofluoric acid (12 mmol HF) is dispersed in 20 ml of diisopentyl ether and is added to the metal isopropylate solution with stirring. Subsequently, the solution is refluxed overnight under nitrogen.

The solvent is removed from the solution by distillation under vacuum.

If desired, any by-products can be removed from the remaining raw product by washing with mall amounts of ethanol as described above or by diafiltration.

End of the explicit synthesis embodiments.

As will be apparent from the above examples, the principle on which the present invention is based can be exploited for very diverse applications in order to prepare a variety of substances that have each specifically selectable properties.

The use of TOP and/or TOPO as solvent during the preparation method has advantages in comparison to the further above mentioned phosphate esters which are, in principle, very suitable. The advantages are a higher synthesis temperature, e.g. approx. 530 Kelvin and higher, and, associated with this, an improved incorporation of the doping agent and, as a result, an increased intensity of the emitted light which can be a crucial factor for the applicability of a fluorescence marker. In addition, at high synthesis temperatures a successful doping of a host lattice can also be achieved even if the atomic size of the dopants matches only badly the ionic size of the host ions. Thus, nearly any fluorescent dye can specifically be made.

Figure 4:
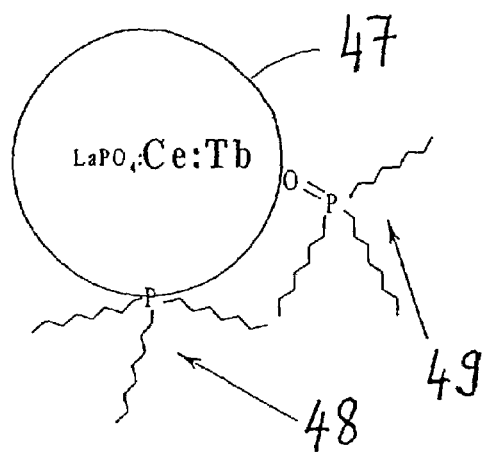
FIG. 4 is a schematic illustration of surface molecules of a doped nanoparticle that has been prepared by the method using the solvent TOP/TOPO.

As is schematically illustrated in FIG. 4, the surface 47 of the nanoparticles is coated immediately after the synthesis by a layer consisting of residual solvent molecules, in particular of trioctylphosphine 48 (abbr. TOP) and trioctylphosphine oxide 49 (abbr. TOPO). The figure shows only one molecule of TOP and TOPO, respectively. This allows a simpler way to handle the nanoparticles after their synthesis, because these surface molecules (residual solvent molecules) cause an improved solubility in standard-solvents without chemically modifying the particles in a second, laborious step.

The substance which is obtained from the above-described steps of the preparation method can, if necessary, be dried also as described above and crumbled to a fine powder up to a mean particle size of approx. 30 nm.

The following paragraph describes detection method and device more in detail with the help of the figures.

Figure 2:
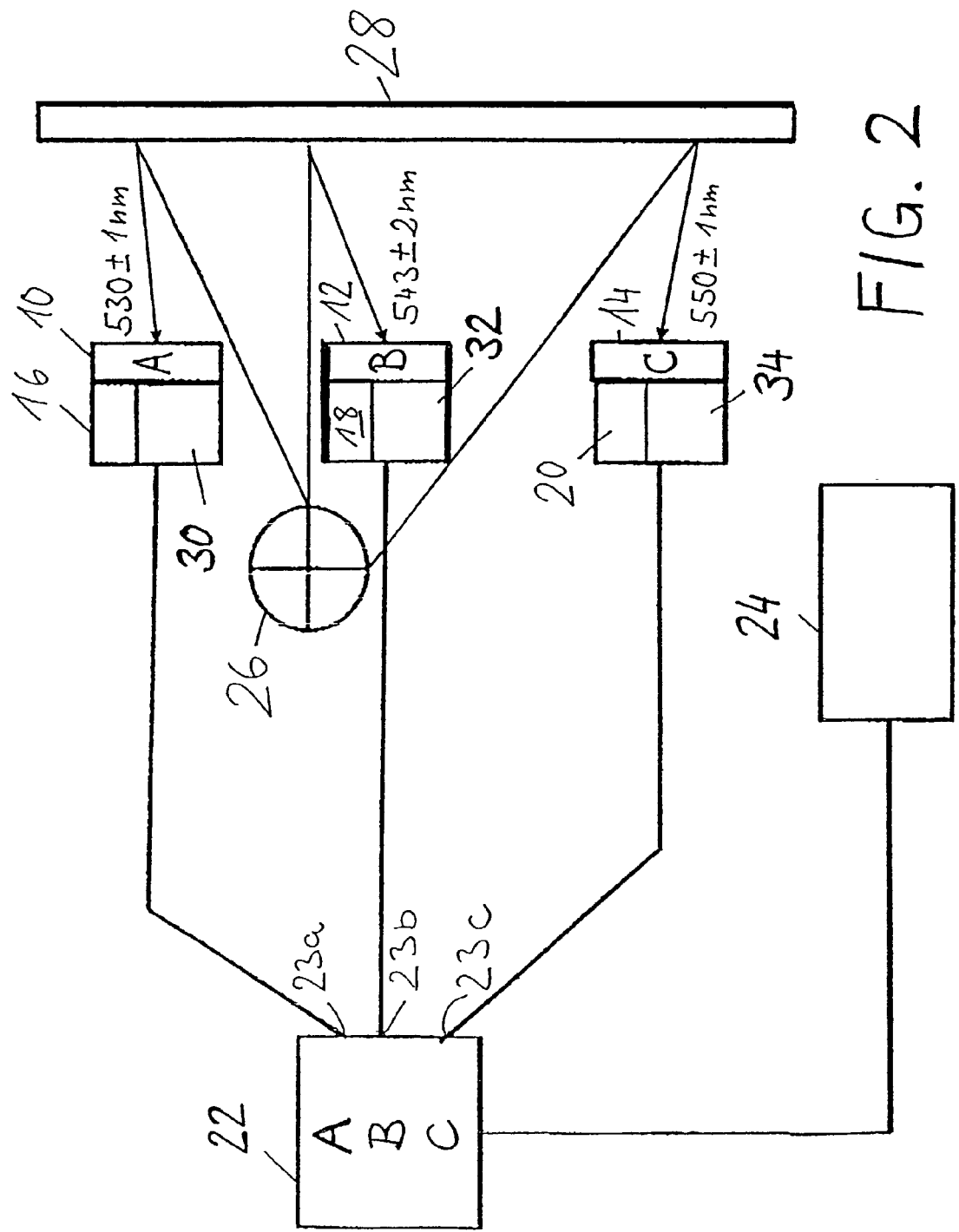
FIG. 2 is a schematic illustration of a circuit diagram according to FIG. 1 showing a more complex version of the detector device.

In all the figures, in particular in FIG. 1 and FIG. 2, the same symbols represent same or functionally equal components.

With general reference to the figures and with particular reference to FIG. 1, a version of a detector device according to the present invention comprises in a basic form three interference filters 10, 12, 14, three photo cells 16, 18, 20, each of which is coupled to an interference filter, an analysing unit 22 for the signals coming from the photo cells, as well as a reading unit 24, for example a display. An energy source 26 in the form of a UV-C light source with a narrow band emission spectrum around 255 nanometers is arranged in such a way that a test substance 28 that shall be examined using the detection method of the invention is illuminated by the light source 26 in an as far as possible shadowless manner.

The test substance 28 shall be examined as to whether a marking is present on it that can be recognized as identical with a predetermined nanoparticle type which itself is characterized by a fluorescence emission main peak.

Figure 5:
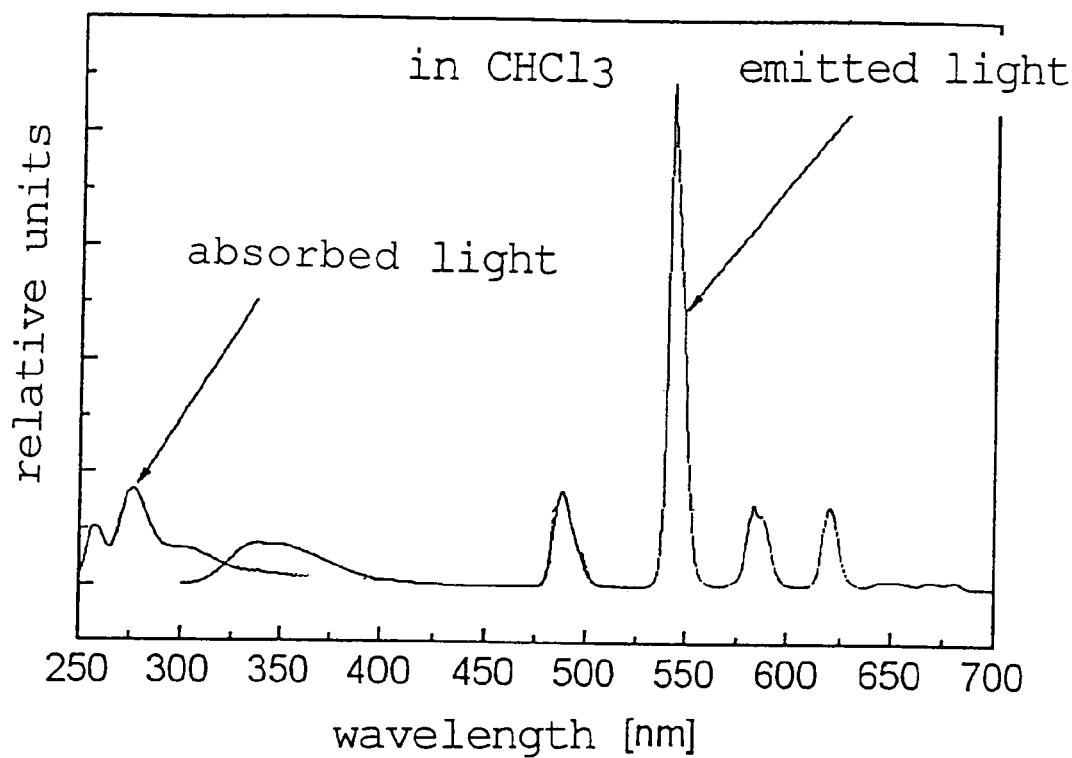
FIG. 5 shows exemplarily the absorption and fluorescence spectrum (excitation wavelength and emission wavelength, resp.) of $LaPO_4Ce:Tb$ in $CHCl_3$.

This predetermined nanoparticle type shall be in the present case $LaPO_4Ce:Tb$, of which the absorption and fluorescence spectra are exemplarily shown in FIG. 5. Details of this illustration are explained further below.

The in FIG. 1 by arrows schematically illustrated radiation excites at first a marking, if present, on the test substance 28 in the form of inorganically doped nanoparticles that are possibly present there. In case the marking emits a certain fluorescence light, which represents a condition for that the test substance may be recognized as authentic, the interference filters 10, 12, and 14 capture certain parts of this fluorescence emission radiation through their respective apertures.

Figure 3:
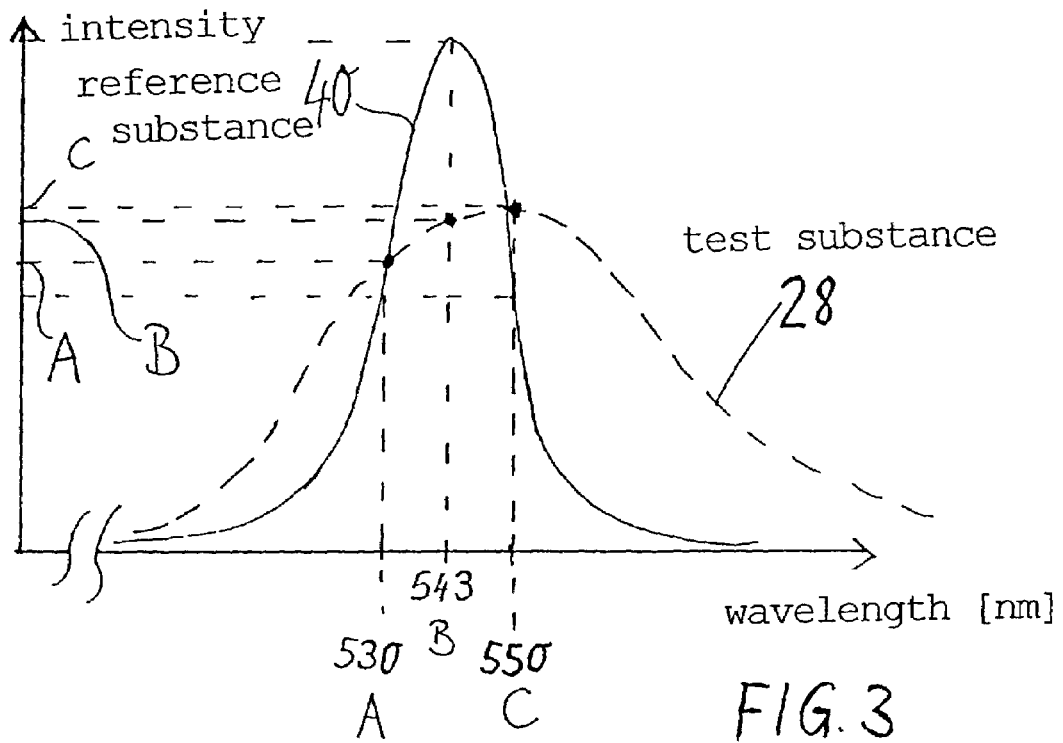
FIG. 3 is a schematic illustration of the emission spectra of a reference substance and a test substance and measurement points of the analysis of the detection.

With reference to FIG. 3 which is only a schematic illustration because the steepness of the main emission peak 40 depicted there does not match the reality, but has been drawn much wider for the purpose of a better comprehensibility, the interference filters 10, 12, and 14 are adjusted so that they allow three 'frequency points' of the emission peak drawn in the figure to pass. In the present case of the terbium fluorescence emission, filter 12 allows only a narrow wavelength region of the maximum of the main peak to pass, that is approximately a wavelength region of 543 nm+/−2 nanometers. The interference filter 10 is adjusted in a way such that it allows a similarly narrow wavelength region to pass. In the present case, it allows a narrow wavelength region of 530+/−10 nanometers, preferred of +/−1 nanometer, to pass and thus it covers the secondary spectral region of the main peak at shorter wavelengths.

The interference filter 14 is adjusted in a manner equivalent to filter 10 and 12 with the only difference that it covers the secondary spectral region at longer wavelengths around 550 nanometers.

With reference back to FIG. 1, the light that passes through the interference filters hits the light-sensitive surface of the photo cells 16, 18, and 20. Depending on the intensity, a more or less large current is produced there which is the larger the more light falls on the photo-sensitive surfaces.

The analysing unit 22 is equipped with three input ports 23a, 23b, 23c which receive the currents coming from the photo cells. The currents from the three photo cells are first digitalized in the analysing unit 22 with a predetermined sample rate of for example 10 kilo hertz and are saved in a memory unit of unit 22 intended for this purpose. This memory is so large that sufficient memory space is available to cover a predetermined time window of the measurement points of, for example, one second or more, if necessary.

Then, in a next step, means of the measurement points during the time window are taken for all three signals from the photo cells 16, 18, and 20. There are now three values. These values are called in the following paragraph A, B, and C. The value A corresponds to the mean of photo cell 16, the value B to that of photo cell 18 and the value C to that of photo cell 20. Now it is checked first whether value B is considerably unequal from zero, that is, whether the test substance has emitted in the narrow region of around 550 nanometers which is the main peak wavelength of the reference substance.

In case a light emission is present, the value B is accepted in an exemplarily chosen range between 50 and 500 as analysable. If the value is lower than 50, it is approved that the test substance emits not enough light in the main peak region, looked at it in absolute terms, in order to be tested by the detection method of the invention with acceptable tolerance. If the value is higher than 500, then it has exceeded the permissible measurement range and cannot immediately be analysed. In such a case the emission light source 26 needs first to be adjusted to a lower intensity. This can be done for example by an automated feed-back between the unit 22 and a controlling unit for the light source 26. However, this connection is not illustrated for reasons of a better clarity.

The value B for the test substance 28 is now between 50 and 500. Thus, it can now be concluded that the test substance emits at least to a certain degree within the narrow wavelength region of the main peak maximum. Thus the test substance 28 could exhibit a marking that is identical with that of the reference substance. In order to establish or to exclude this possibility, two relations (ratios) are then taken: A/B and C/B. That is, each of the intensities of the secondary spectral regions coming from the photo cells 16 and 20 are put in relation to the intensity of the main peak.

According to the invention, the sample is only then approved to be authentic when both relations are below a predetermined threshold value. Because only in that case an emission spectrum of the test substance is present that has a similarly sharp emission main peak compared to that of the reference substance. As soon as at least one of the two above-named ratios is greater than this threshold value, the sample is classified as non-authentic, and an appropriate output is produced in the display unit 24. For the result of identity, an appropriate output is also produced.

The level of the threshold value can advantageously be in rough approximation around 50%, if each of the secondary spectral regions have been measured at a wavelength that corresponds to the width at half-height of the reference peak.

For example, in case the result for B is the value 300, the test substance is verified only then as authentic, if A as well as C are below a value of 150. To make sure, a certain range of tolerance can be defined in one or the other direction.

The advantage of analysing relations of intensities instead of absolute values is that the method is thus independent of the absolute values of the recorded intensity of radiation. Thus a preceding calibration is mostly not necessary, and the distance between sample and filters can vary within certain limits without causing a false result, as long as it is guaranteed that the distances between the three filters to the surface of the test substance are equal.

The analysis of the broken emission line of test substance 28 given in FIG. 3 would result in about 90% for the relation A/B and about 105% for C/B. Thus it is undoubtedly demonstrated that the test substance is 'not identical'.

The illustration given in FIG. 2 shall explain the detection method of the invention and the corresponding device in a more complex variant.

The set-up is basically the same as illustrated in FIG. 1. The set-up drawn in FIG. 2, however, differs basically in that instead of photo cells CCD cameras 30, 32, and 34, are now coupled instead of or in conjunction with the photo cells to the interference filters 10, 12, and 14. In case of a simultaneous coupling, the following description of the method steps can be carried out in addition to those described above in order to allow an additional checking of the marking. In this case, after having passed the first test (see above) successfully, the images recorded by the CCD cameras are compared with a predetermined reference pattern that is present as a bitmap in the memory unit of the analysing unit 22 provided for this purpose by using pattern recognizing algorithms as known in prior art. Only if there is a great matching of the patterns which may be defined from case to case, the test substance is recognized to be authentic, and an appropriate output is shown on the display 24.

In the other case, if apart from the CCD cameras none of the photosensitive elements receive the light of the interference filters, the luminescence density of the images recorded by the CCD cameras is analysed according to the above-described quantification of the signals with subsequent formation of a quotient. It goes without saying that this method can be carried out separately for individual areas of the CCD camera images from which a corresponding mean and a corresponding result, respectively, can be obtained.

Although the present invention has been described in conjunction with a preferred embodiment thereof, it is not limited to this example but can be modified in many different ways.

In particular, UV-light absorbing substances of the invention can be used to screen off or to eliminate UV-light or as converter to visible light. Thus, they can for example be used as addition to sun protecting cremes, or they increase as a coating substance the efficiency of solar cell systems, in particular of photovoltaic systems, and protect the systems from premature ageing caused by UV-light.

The use of nanoparticles, comprising one or more substances of the family of phosphors, in particular of tungstates, tantalates, gallates, aluminates, borates, vanadates, sulphoxides, silicates, and of halide compounds, opens also a new, diverse field of application for the substance groups of the invention, namely the generation of light in devices or any lighting bodies as well as in lamps. Thus, they can advantageously be fitted to standard LEDs, any display devices, and all kinds of screens. However, the use of these 'nano-phosphors' particularly presents itself, if the special properties of the nanoparticles offer any special advantage that is typical for the particular case of application. Only exemplarily named are large, luminescent, possibly three-dimensionally built areas or luminescent devices which are then only allowed to be economically manufactured by adding nanoparticles to thin films. Equally, doped nanoparticles in a general sense and the inorganically doped nanoparticles that are specifically further developed according to the present invention can be used for the generation of light.

What is claimed is:

1. A method for synthesizing metal salt nanoparticles containing an anion comprising phosphates, halophosphates, arsenates, sulphates, germanates, vanadates, tantalates, tungstenates, molybdates, alkalihalogenates, or other halides, said method comprising:
   a) preparing a synthesis mixture, at least from
   aa) one organic component coordinating solvent controlling the crystal growth of the nanoparticles, which comprises phosphororganic compounds, monoalkylamines or dialkylamines, and a solvent for the organic component controlling the crystal growth,
   bb) a cation starting material which serves as cation source in the synthesis mixture, and
   cc) an anion starting material that serves as anion source, which comprises:
   aaa) free acids of the salts of the particular metal salt nanoparticles which are to be prepared, or
   bbb) salts, or
   ccc) organic compounds which release the anion at the synthesis temperature, and
   b) reacting the synthesis mixture until said nanoparticles have formed.

2. The method according to claim 1, wherein the monoalkylamine comprises dodecylamine, and the dialkylamine comprises bis(ethylhexyl)amine.

3. The method according to claim 1, wherein said phosphororganic compound is selected from:
   a) esters of phosphinic acid, ((R1-)(R2-)(R3-O—)P=O),
   b) diesters of phosphonic acid, ((R1-)(R2—O—)(R3—O—)P=O),
   c) triesters of phosphoric acid (trialkyl phosphates), ((R1O—)(R2-O—)(R3-O—)P=O),
   d) trialkyl phosphines, ((R1-)(R2-)(R3-)P),
   e) trialkyl phosphine oxides, ((R1-)(R2-)(R3-)P=O),
   wherein R1, R2, R3 are branched or unbranched alkane chains comprising at least one carbon atom, or phenyl, tolyl, xylyl, or benzyl groups,
   f) a phosphoric amide, and
   g) a phosphoric amide oxide.

4. The method according to claim 3, wherein R1, R2, or R3 are branched or unbranched alkane chains which carry at least one of the following groups:
   carboxyl group (—COOH), carboxylic acid ester group (—COOR), amino groups (—NH$_2$) and (—NHR), hydroxyl group (—OH), cyano group (—CN), mercapto group (—SH), bromine (—Br) and chlorine (—Cl), or combinations of these groups.

5. The method according to claim 3, wherein a trialkyl phosphate or a trialkyl phosphine is used as a growth controlling component for the preparation of nanoparticles, and wherein per mol metal ions less than 10 mol of the growth controlling component is used.

6. The method according to claim 5, wherein per mol metal ions of 0.9 to 5 mol of the growth controlling component is used.

7. The method according to claim 6, wherein per mol metal ions of 0.95 to 2 mol of the growth controlling component is used.

8. The method according to claim 1, wherein said solvent is selected from at least one of a) an ether compound and b) an alkane compound that boils above the synthesis minimum temperature.

9. The method according to claim 8, wherein said a) ether compound comprises dipentyl ether, dihexyl ether, diheptyl ether, dioctyl ether, dibenzyl ether, diisoamyl ether, ethylene glycol dibutyl ether, diethylene glycol dibutyl ether, or diphenyl ether, and said b) alkane compound that boils above the synthesis minimum temperature comprises dodecane or hexadecane.

10. The method according to claim 1 further comprising neutralizing the synthesis mixture using a base that is soluble in the synthesis mixture.

11. The method according to claim 1 wherein the cation source comprises at least one of metal chlorides, metal alkoxides, bromides, iodides, acetylacetonate and metal acetates.

12. The method according to claim 1, wherein the anion source comprises salts having an organic cation or alkali metal salts.

13. The method according to claim 1, wherein phosphoric acid is used as anion source for the preparation of nanoparticles with phosphorus-containing anions, boric acid is used as anion source for the preparation of nanoparticles with boron-containing anions, and hydrofluoric acid is used as anion source for the preparation of nanoparticles with fluorine-containing anions.

14. Nanoparticles being obtainable by the method of claim 1, and containing an anion comprising phosphates, halophosphates, arsenates, sulphates, germanates, vanadates, tantalates, tungstenates, molybdates, alkalihalogenates, or other halides, said nanoparticles having a surface modified with at least one coordinating organic solvent selected from phosphororganic compounds, monoalkylamines or dialkylamines and having a mean particle size of up to approximately 30 nm.

15. The nanoparticles according to claim 14, wherein the nanoparticles are phosphors.

16. The nanoparticles according to claim 15, comprising a lanthanum or lanthanide compound as a host lattice, and wherein dopants of the group of lanthanides are contained.

17. The nanoparticles according to claim 16, wherein cerium and terbium are used for doping and LaPO$_4$ as host material.

18. The nanoparticles according to claim 14, wherein the nanoparticles have a size of 1 to 8 nm, with a standard deviation of less than 30%.

19. The nanoparticles according to claim 14 comprising nanoparticles which are selected from the substance group consisting of rare earth metal phosphates, or IIIrd main group phosphates, or phosphates of calcium (Ca), strontium (Sr), or barium (Ba), wherein the nanoparticles have a size, measured along their longest axis, of maximally 15 nm, with a standard deviation of less than 30.

20. The nanoparticles according to claim 19 wherein the nanoparticles have a size, measured along their longest axis, of maximally 10 nm.

21. The method according to claim 10 wherein the base that is soluble in the synthesis mixture comprises trihexylamine, triheptylamine, trioctylamine or tris(2-ethylhexyl)amine.

22. A method for synthesizing metal salt nanoparticles containing an anion comprising phosphates, halophosphates, arsenates, suiphates, germanates, vanadates, tantalates, tungstenates, molybdates, alkalihalogenates, or other halides,
said method comprising:
a) preparing a synthesis mixture, at least from
aa) one coordinating organic solvent selected from phosphoric acid triesters, phosphoric amides, phosphoric amide oxide, trialkyl phosphines and trialkyl phosphine oxides,
bb) a cation source,
cc) an anion source, and
b) reacting the synthesis mixture until said nanoparticles have formed.

23. The method according to claim 22, wherein the coordinating solvent is a phosphoric acid triester.

24. The method according to claim 23, wherein the phosphoric acid triester is trisethylhexylphosphate.

25. The method according to claim 22, wherein the coordinating solvent is comprises at least one of trisoctylphosphine (TOP) and trisoctyphosphine oxide (TOPO).

26. The method according to claim 22, wherein the metal salt nanoparticles to be synthesized are metal phosphate particles, the cation source is a metal chloride, the anion source is phosphoric acid or a metal phosphate salt and the reaction is conducted in the presence of an acid scavenger.

27. The method according to claim 23, wherein the metal salt nanoparticles to be synthesized are metal phosphate particles, the cation source is a metal chloride, the anion starting material is phosphoric acid or a metal phosphate salt and the reaction is conducted in the presence of an acid scavenger.

28. The method according to claim 26, wherein the acid scavenger is an amine.

29. The method according to claim 27, wherein the acid scavenger is an amine.

30. Nanoparticles being obtainable by the process of claim 23 and containing an anion comprising phosphates, halophosphates, arsenates, sulphates, germanates, vanadates, tantalates, tungstenates, molybdates, alkalihalogenates, or other halides, said nanoparticles having a surface modified with at least one coordinating organic solvent selected from phosphoric acid triesters, phosphoric amides, phosphoric amide oxides, trialkyl phosphines and trialkyl phosphine oxides and having a mean particle size of up to approximately 30 nm.

31. Nanoparticles being obtainable by the process of claim 24 and containing an anion comprising phosphates, halophosphates, arsenates, sulphates, germanates, vanadates, tantalates, tungstenates, molybdates, alkalihalogenates, or other halides, said nanoparticles having a surface modified with at least one phosphoric acid triester and having a mean particle size of up to approximately 30 nm.

32. Metal phosphate nanoparticles obtainable by the process of claim 27, said nanoparticles having a surface modified with at least one phosphoric acid triester and having a mean particle size of up to approximately 30 nm.

33. The metal phosphate nanoparticles of claim 32 which are doped.

34. The metal phosphate nanoparticles of claim 33 of having LaPO$_4$ as host structure.

35. The metal phosphate nanoparticles of claim 34 being LaPO$_4$; Ce: Tb.

36. Nanoparticles of claim 31, wherein the nanoparticles have a size of 1 to 8 nm with a standard deviation of less than 30 %.

37. Nanoparticles of claim 36, wherein the nanoparticles have a size of 4 to 5 nm.

38. Nanoparticles of claim 36, wherein the standard deviation is less than 10%.

39. Nanoparticles of claim 37, wherein the standard deviation is less than 10%.

40. A detection method to recognize fluorescence of a test substance as identical with fluorescence of a reference substance comprising nanoparticles according to claim 30 having a fluorescence emission main peak, comprising:
determining a fluorescence emission main peak of the reference substance comprising nanoparticles according to claim 30;

exciting the test substance using an excitation method;

filtering the spectral region of the main peak of the test substance;

filtering at least one secondary spectral region next to the main peak, where relatively to the intensity of the main peak a low or not any intensity is expected for the reference substance;

quantifying the filtered emission intensities within the spectral regions;

determining at least one relation of the filtered emission intensities to each other; and evaluating correspondence of the test substance with the reference substance on a basis of the at least one relation.

41. The detection method according to claim 40, wherein apart from the main peak at least two of secondary spectral regions are filtered and evaluated.

* * * * *